(12) United States Patent
Sun et al.

(10) Patent No.: US 7,053,193 B2
(45) Date of Patent: May 30, 2006

(54) BREAST CANCER TRANSCRIPTION FACTOR GENE AND USES

(75) Inventors: Zairen Sun, Rockville, MD (US); Wufang Fan, Germantown, MD (US); Karl F. Kovacs, Rockville, MD (US); Xuan Li, Silver Spring, MD (US); Gilbert Jay, North Bethesda, MD (US)

(73) Assignee: Origene Technologies, Inc., Rockville, MD (US)

( * ) Notice: Subject to any disclaimer, the term of this patent is extended or adjusted under 35 U.S.C. 154(b) by 39 days.

(21) Appl. No.: 10/054,935

(22) Filed: Jan. 25, 2002

(65) Prior Publication Data

US 2003/0143546 A1   Jul. 31, 2003

(51) Int. Cl.
*C07H 21/04* (2006.01)

(52) U.S. Cl. .................................... 536/23.1
(58) Field of Classification Search ............... 536/23.1
See application file for complete search history.

(56) References Cited

U.S. PATENT DOCUMENTS 5,912,143 A * 6/1999 Bandman et al.

OTHER PUBLICATIONS

Thompson et al (GEnome Research, 2002, 12:1517-1622.*
Soares et al PNAS, 1994, 91:9228-9322).*
Yerushalmi et al 9Gene, 2001, 263:55-60).*
Caillou et al (J. Clinical Endocrinology and Metabolism, 2001, 86:335 '-335').*
Sambrook (A Laboratory Manual, 2nd Ed., Sambrook et al, Eds, 1989, Cold Spring Harbor Laboratory Press, p. .6).*
Old and Primrose (Principles of Gene Manipulation, An Introduction to Genetic Engineering, 1989, Blackwell Scientific Publications, Osney Mead, Oxfor, p. 122.*
Jansen et al., 1995, Pediatric Research, 37(6):681-686).*
Alberts et al (Molecular Biology of the Cell, 3rd Ed., 1994, p. 465).*
Shantz and Pegg (Int. J. Biochem and Cell Biol., 1999, 31:107-122).*
Fu et al (EMBO J. 1996, 15:4392-4401).*
Brennan et al (J. Autoimunity, 1989, 2 suppl:177-186).*
Zimmer (Cell Motility and the Cytoskeleton, 1991, 20:325-337).*
Eriksson et al (Diabetologia, 1992, 35:143-147).*
Hell et al (Lab. Invest., 1995, 73:492-496).*
Powell et al (Pharmacogenesis, 1998, 8:411-421).*
Carrere et al (Gut, 1999, 44:550-551).*
Vallejo et al (Biochimie, 2000, 82:1129-1133).*
Guo et al (J. Pharm. Exp. Therapeutics, 2002, 300,:206-212).*
Jang et al 9Clinical and Experimental Metastasis, 1997, 15:469-483).*
Bork (Genome Research, 2000, 10:398-400).*
Scottt et al (Nature Genetics, 1999, 21:440-443).*
Bowie et al (Science, 1990, 257:1306-1310).*
Burgess et al (j. Cell Bio., 1990, 111::2129-2138).*
Lazar et al (Mol. Cell. Biol., 1988, 8:1247-1252).*
Harris et al (J. Am. Soc. Nephrology, 1995, 6:1125-1133).*
Ahn et al (Nature Genetics, 1993, 3(4):283-291).*
Cawthon et al (Genomics, 1991, 9(3):446-460).*
Konno et al (Al049450)Genbank Sequence Database, National Center for Biotechnology Information, National Library of Medicine, Bethesda, Maryland, publicly available Jun. 23, 2000).*
Boehringer Mannheim Biochemicals, 1994, Catalog, p. 93.*
Carninci et al (GEnome Research, 2000, 10(10)1617-1630).*
Shibata et al (Genome Research, 2000, 10(1)1757-1771).*
Reiger et al (Glossary of Genetics and togenetics, Classical and Molecular, 4th Ed., Springer-Verlag, Berline, 1976, p. 17).*
XM_058887. NCBI Sequence Revision History and Sequence Record Dated Dec. 10, 2001.
AK014463. NCBI Sequence Revision History and Sequence Record Dated Jan. 19, 2002.

* cited by examiner

*Primary Examiner*—Susan Ungar
(74) *Attorney, Agent, or Firm*—Millen, White, Zelano & Branigan, P.C.

(57) ABSTRACT

The present invention relates to all facets of novel polynucleotides, the polypeptides they encode, antibodies and specific binding partners thereto, and their applications to research, diagnosis, drug discovery, therapy, clinical medicine, forensic science and medicine, etc. The polynucleotides, Urb-ctf, are expressed in breast cancer and are therefore useful in variety of ways, including, but not limited to, as molecular markers, as drug targets, and for detecting, diagnosing, staging, monitoring, prognosticating, preventing or treating, determining predisposition to, etc., diseases and conditions especially related to breast cancer.

15 Claims, 1 Drawing Sheet

```
              *        20         *        40         *        60
BCU1041    : MTMRSAVKAAAAPAGGNPEGLLDYEAAALGGPSDLPSAAEAELPHRKLKEEGPPLA :  60
AK_014463  : MTMRSATKAAAAPAGGNPEGRLDYEPAAALGGPEDSSAAEAELPERHRKTKEEGPPLA :  60
XM_058887  : -------------------------------------------------------- :   -

*        80         *       100         *       120
BCU1041    : SSGGGSPAASPAGGGGSGKGRGLLLPAGALDGGQPESWGGSVPLECPPATKGAGTSGEEA : 119
AK_014463  : SSQGGSESPSPASCGGGKGRGLLLPAGAARGQDPSWGGSVPLECPEATKQAGTCGDEV : 120
XM_058887  : -------------------------------------------------------- :   -

*       140         *       160         *       180
BCU1041    : AAGAGGSPRKYGAVLRIQEGSIL-AAAKEETEWAGUKGAASPAATASDPAGPPELPLP : 178
AK_014463  : AAGAGGSPRKYQAVLPETGSIVVAAAEPPTPWAGDKGCAASPAAIAEDPAGPPELPLP : 180
XM_058887  : -------------------------------------------------------- :   -

*       200         *       220         *       240
BCU1041    : GPPPLAPTATAGTLAASEGRWKSTKSPLGGGGGSGASSQAHLKQILLGLDLIEQQGG : 238
AK_014463  : GPPPLAPTATAGTLAASEGRWKSTIKSPLGGGGGSGASSQAHLKQILLQLDLIEQQGG : 240
XM_058887  : -------------------------------------------------------- :   -

*       260         *       280         *       300
BCU1041    : QLQAKEEELEELKSERDTLLAELEPMERRMQLVKKDNEKERHKLIQGYEIEEREEIELSE : 298
AK_014463  : QLQAKELEELKSERDTLIAELERMERRMQLVKRDNEKERHKLLQGYEPEEREEAELSE : 300
XM_058887  : ------------------------MERRMQLVKKDNEKERHKLIQGYEIEEREEIELSE :  35

*       320         *       340         *       360
BCU1041    : KIKLEEQPELGETSQILPEKPFSCGRSGKGHKRKSPFGSTERKIPVKKLAPEFSKVKTKT : 358
AK_014463  : KIKLERQPELGETSQALPSKPFSCGRSGKGHKRKTPFGNTERKNPVKKLAPEFSKVKTKT : 360
XM_058887  : KIKLEEQPELGETSQILPEKPFSCGRSGKGHKRKSPFGSTERKIPVKKLAPEFSKVKTKT :  95

*       380         *       400         *       420
BCU1041    : PKHSPIKEEPCGSLSETVCKRELRSQETPEKPRSSVDTPPRLSTPQKGPSTHPKEKAFSS : 418
AK_014463  : PKHSPIKEEPCGSISETVCKRELRSQETPEKPRSSVDTPPRLSTPQKGPSTHPKEKAFSS : 420
XM_058887  : PKHSPIKEEPCGSLSETVCKRELRSQETPEKPRSSVDTPPRLSTPQKGPSTHPKEKAFSS : 155

*       440         *       460         *       480
BCU1041    : EIEDLPYLSTTEMYLCRWHQPPPSPLPLRESSPKKEETVAEGIMESSVAGETSVLAVPSG : 478
AK_014463  : EMEDLPYLSTTEMYLCRWHQPPPSPLPLRESSPKKEETVAEGIMESSVAGETSVIAVPSG : 480
XM_058887  : EIEDLPYLSTTEMYLCRWHQPPPSPLPLRESSPKKEETVASKA---------------- : 198

*       500         *       520         *       540
BCU1041    : RDHSVEPLRDEPRSDLLENLDDSVESKRHAKLELDEKRRKEWDIQRIREQRILQRLQLRN : 538
AK_014463  : RDHSVEELRDPNPSDIILENLDDSVESKRHAKLELDEKRRKEWDIQRIREQRILQRLQLRN : 540
XM_058887  : -------------------------------------------------------- :   -

*       560         *       580         *       600
BCU1041    : KINKGICESIDSVTSESPEDDVESLMITPELAVAGESGPLPKITLNEELPWLDERSEG : 598
AK_014463  : KKKGIQESEPEVTSEPEDDVESLIEPPLPVAGGRPLPKIAGNEELPWLDERSEG : 600
XM_058887  : -------------------------------------------------------- :   -

*       620         *       640         *       660
BCU1041    : RLELQKSQGPRLTCKN--------------------------------- : 614
AK_014463  : RLELICKHGPIRLEKN--------------------------------- : 616
XM_058887  : ------------------------------------------------- :   -
```

Figure 1

BREAST CANCER TRANSCRIPTION FACTOR GENE AND USES

DESCRIPTION OF THE DRAWINGS

FIG. 1 shows amino acid alignments between Urb-ctf ("BCU1041," SEQ ID NO 2), AK014463 (mouse, SEQ ID NO 4) and XM_058887 (human, SEQ ID NO 3). Regions of sequence identity are shaded.

DESCRIPTION OF THE INVENTION

The present invention relates to all facets of Urb-ctf, polypeptides encoded by it, antibodies and specific binding partners thereto, and their applications to research, diagnosis, drug discovery, therapy, clinical medicine, forensic science and medicine, etc. Urb-ctf polynucleotides, polypeptides, antibodies, etc., are useful in variety of ways, including, but not limited to, as a molecular markers, as drug targets, and for detecting, diagnosing, staging, monitoring, prognosticating, preventing or treating, determining predisposition to, etc., diseases and conditions, such as breast cancer. The identification of specific genes, and groups of genes, expressed in pathways physiologically relevant to breast cancer permits the definition of functional and disease pathways, and the delineation of targets in these pathways which are useful in diagnostic, therapeutic, and clinical applications. The present invention also relates to methods of using the polynucleotides and related products (proteins, antibodies, etc.) in business and computer-related methods, e.g., advertising, displaying, offering, selling, etc., such products for sale, commercial use, licensing, etc.

Breast cancer is the second leading cause of cancer death for all women (after lung cancer), and the leading overall cause of death in women between the ages of 40 and 55. In 2000, several hundred thousand new cases of female invasive breast cancer were diagnosed, and about 40,000 women died from the disease. Nearly 43,000 cases of female in situ (preinvasive) breast cancer were diagnosed in 2000.

There is not one single disease that can be called breast cancer. Instead, it is highly heterogeneous, exhibiting a wide range of different phenotypes and genotypes. No single gene or protein has been identified which is responsible for the etiology of all breast cancers. A number of different genes have already been identified which are associated with breast cancer, or a predisposition to it. It is likely that diagnostic and prognostic markers for breast cancer disease will involve the identification and use of many different genes and gene products to reflect its multifactorial origin.

A continuing goal is to characterize the gene expression patterns of the various breast carcinomas in order to genetically differentiate them, providing important guidance in preventing, diagnosing, and treating cancer. For instance, the c-erb-B2 gene codes for a transmembrane protein which is over-expressed in about 20–30% of all breast cancers. Based on this information, immunotherapy using an anti-c-erb-B2 antibody has been developed and successfully used to treat breast cancer. See, e.g., Pegram and Slamon, Semin Oncol., 5, Suppl 9:13, 2000. Molecular pictures of cancer, such as the pattern of up-regulated genes identified herein, provide an important tool for molecularly dissecting and classifying cancer, identifying drug targets, providing prognosis and therapeutic information, etc. For instance, an array of polynucleotides corresponding to genes differentially regulated in breast cancer can be used to screen tissue samples for the existence of cancer, to categorize the cancer (e.g., by the particular pattern observed), to grade the cancer (e.g., by the number of up-regulated genes and their levels of expression), to identify the source of a secondary tumor, to screen for metastatic cells, etc. These arrays can be used in combination with other markers, e.g., keratin immunophenotyping (e.g., CK 5/6), c-erb-B2, estrogen receptor (ER) status, etc., or any grading system desired.

Urb-ctf

Urb-ctf ("Up-Regulated Breast Cancer Transcription Factor" or BCU1041FB or FB2847A11) codes for a transcription regulatory factor having 614 amino acids which is up-regulated in breast cancer. The nucleotide and amino acid sequences of Urb-ctf are shown in SEQ ID NOS 1 and 2. It contains a bZIP domain at about amino acid positions 228–275, conferring DNA-binding activity. It also has a leucine zipper providing a dimerization activity. There are a number of UniGene clusters that map close to the gene, including, e.g., Hs.350229, Hs.272458, Hs.350229, Hs.255286, Hs.184779, and Hs.276916. Predictions using GenomeScan (e.g., Yeh et al., Genome Res. 11: 803–816, 2001) revealed at least two different predicted genes, Hs17_11001_27_4_1 and Hs17_11001_27_5_2, instead of the single gene, Urb-ctf, described herein. A partial human cDNA (AL049450; XM_058887; SEQ ID NO 3) for Urb-ctf was previously identified, but this coded for only 198 amino acids and contained only a part of the bZIP domain, as well as missing significant portions of the N- and C-termini. A mouse homolog, AK_014463 (SEQ ID NO 4), has been cloned.

All or part of Urb-ctf is located in genomic DNA represented by GenBank ID: AC068669, BAC-ID: RP11-749I16, and Contig ID: NT_010844. The present invention relates to any isolated introns and exons that are present in the gene. Intron and exon boundaries can be routinely determined, e.g., using the polypeptide and genomic sequences disclosed herein. Using UniSTS probes, Urb-ctf can be chromosomally mapped at its 5' end with UniSTS: 155813 to 40.144 Mb, and its 3' end with UniSTS: 619 to 40.084 Mb. Strikingly, the Urb-ctf overlaps with the thyroid hormone receptor alpha 2 gene (CAB57886).

As indicated by the presence of a bZIP domain, Urb-ctf has transcriptional regulatory activity, DNA-binding activity, and dimerization activity. These activities can be determined routinely. For example, DNA-binding activity can be determined using gel-shift assays, e.g., as carried out in, e.g., U.S. Pat. Nos. 6,333,407 and 5,789,538. Transcriptional activity can be determined using conventional transcriptional assays, including in vivo and in vitro assays, such as those described in F. M. Ausubel et al., Eds., CURRENT PROTOCOLS IN MOLECULAR BIOLOGY (John Wiley & Sons, New York, 1994); de Wet et al., Mol. Cell Biol. 7:725 (1987); U.S. Pat. No. 6,306,649; U.S. Pat. No. 6,214,588; Liao, S. M. et al., Genes. Dev. 5:2431–2440 (1991); Nonet, M., et al., Cell 50:909–915 (1987). The phrase "transcriptional regulatory activity" indicates that the polypeptide modulates transcription in analogy to the activity of other bZIP proteins, e.g., by binding to DNA and interacting with other proteins of the transcription apparatus. For example, both c-Jun and c-Fos are bZIP proteins that form a dimer known as the transcriptional activator AP-1, a transcriptional activator. See, e.g., Genes VII, Lewin, Pages 649–665, 2000. Dimerization activity, i.e., the ability to form hetero- or homodimers with other proteins (in analogy to the c-fos and c-jun system), can be measured routinely, e.g., using the yeast two-hybrid system.

Nucleic acids of the present invention map to chromosomal band 17q21.1. There are a number of different disorders which have been mapped to, or in close proximity to, this chromosome location. These include, e.g., Dementia, frontotemporal, with parkinsonism; Neuroblastoma; Osteoporosis, idiopathic; Ehlers-Danlos syndrome, types I and VIIA; Osteogenesis imperfecta; Glanzmann thrombasthenia, type B; Renal cell carcinoma, papillary; Thrombocytopenia, neonatal alloimmune; Trichodontoosseous syndrome; Hypertension; Epidermolytic hyperkeratosis; Hemolytic anemia due to band 3 defect; Spherocytosis, hereditary; Gliosis, familial progressive subcortical; Renal tubular acidosis, distal; Patella aplasia or hypoplasia; and Pseudohypoaldosteronism type II. Nucleic acids of the present invention can be used as linkage markers, diagnostic targets, therapeutic targets, for any of the mentioned disorders, as well as any disorders or genes mapping in proximity to it.

In addition to its expression in breast cancer, Urb-ctf can be detected in most tissues examined, but either none, or at very low levels, in normal breast tissue. Multiple forms of it can be detected in the brain, muscle, testes, and thymus. As these results indicate, Urb-ctf has a normal functional role in most tissues, and can consequently be involved with diseases associated with them, as well. For instance, Urb-ctf can be involved in renal cell carcinoma and familial gliosis disease. As discussed earlier, no single gene is responsible for all breast cancers. Thus, the fact that Urb-ctf is up-regulated in the breast cancers examined herein does necessarily mean that it will be up-regulated in all human breast cancers.

Urb-ctf can be utilized in a number of different ways. Because it is up-regulated in breast cancers, it can be used as a marker to determine the presence of breast cancer in normal breast tissue for diagnostic and therapeutic applications. Methods for detecting Urb-ctf nucleic acid and polypeptide are described in more detail below. It can also be used as a therapeutic target, e.g., by down-regulating or suppressing expression of Urb-ctf, either at the nucleic acid or protein level. For example, the cancer can be treated by administering effective amounts of anti-sense to block expression of the gene. Inhibition of the protein's functional activity can also be achieved. For example, polyamides, such as those described in Bremer et al., *Bioorganic Med. Chem.*, 9:2093–2103, 2001, can be used to inhibit binding of Urb-ctf to DNA. Specificity to breast cancer cells can be achieved by conjugating the polyamide, or other therapeutic agent, to a breast cancer marker, such as c-erb-B2.

Urb-ctf polypeptide and gene can also be used in transcriptional assays, such as the yeast two-hybrid system. Rather than using the DNA-binding domain of GAL4, Urb-ctf can be used as the fusion partner for a protein whose binding partner is to be identified. See, e.g., Allen et al., *TIBS*, December 1995, Pages 511–516. DNA sequences to which Urb-ctf and other bZIP proteins bind are disclosed, e.g., in Kise and Shin, *Bioorganic Med. Chem.*, 9:2485–2491, 2001.

As illustrated in FIG. 1, Urb-ctf is highly conserved between human and mouse with about 97% amino acid sequence identity between the two proteins, about 93% nucleotide sequence similarity. The variations between the polypeptides, e.g., at about amino acid positions 38, 68, and 77, are evidently amino acids which are not stringently required for biological activity, and therefore can provide guidance in the kind of mutations/polymorphisms that can be made without eliminating the activity of the protein.

Nucleic Acids

A mammalian polynucleotide, or fragment thereof of the present invention is a polynucleotide having a nucleotide sequence obtainable from a natural source, i.e., the species name indicates that the polynucleotide or polypeptide is obtainable from a natural source. It therefore includes naturally-occurring normal, naturally-occurring mutant, and naturally-occurring polymorphic alleles (e.g., SNPs), differentially-spliced transcripts, splice-variants, etc. By the term "naturally-occurring," it is meant that the polynucleotide is obtainable from a natural source, e.g., animal tissue and cells, body fluids, tissue culture cells, forensic samples. Natural sources include, e.g., living cells obtained from tissues and whole organisms, tumors, cultured cell lines, including primary and immortalized cell lines. Naturally-occurring mutations can include deletions (e.g., a truncated amino- or carboxy-terminus), substitutions, inversions, or additions of nucleotide sequence. These genes can be detected and isolated by polynucleotide hybridization according to methods which one skilled in the art would know, e.g., as discussed below.

A polynucleotide according to the present invention can be obtained from a variety of different sources. It can be obtained from DNA or RNA, such as polyadenylated mRNA or total RNA, e.g., isolated from tissues, cells, or whole organism. The polynucleotide can be obtained directly from DNA or RNA, from a cDNA library, from a genomic library, etc. The polynucleotide can be obtained from a cell or tissue (e.g., from an embryonic or adult tissues) at a particular stage of development, having a desired genotype, phenotype, disease status, etc. A polynucleotide which "codes without interruption" refers to a polynucleotide having a continuous open reading frame ("ORF") as compared to an ORF which is interrupted by introns or other noncoding sequences.

Polynucleotides and polypeptides (including any part of Urb-ctf) can be excluded as compositions from the present invention if, e.g., listed in a publicly available databases on the day this application was filed and/or disclosed in a patent application having an earlier filing or priority date than this application and/or conceived and/or reduced to practice earlier than a polynucleotide in this application.

As described herein, the phrase "an isolated polynucleotide which is SEQ ID NO," or "an isolated polynucleotide which is selected from SEQ ID NO," refers to an isolated nucleic acid molecule from which the recited sequence was derived (e.g., a cDNA derived from mRNA; cDNA derived from genomic DNA). Because of sequencing errors, typographical errors, etc., the actual naturally-occurring sequence may differ from a SEQ ID listed herein. Thus, the phrase indicates the specific molecule from which the sequence was derived, rather than a molecule having that exact recited nucleotide sequence, analogously to how a culture depository number refers to a specific cloned fragment in a cryotube.

As explained in more detail below, a polynucleotide sequence of the invention can contain the complete sequence as shown in SEQ ID NO 1, degenerate sequences thereof, anti-sense, muteins thereof, genes comprising said sequences, full-length cDNAs comprising said sequences, complete genomic sequences, fragments thereof, homologs, primers, nucleic acid molecules which hybridize thereto, derivatives thereof, etc.

The present invention also relates to an isolated polynucleotide which is specific for human Urb-ctf and which codes for a polypeptide, said polypeptide comprising, e.g., amino acid 38 of SEQ ID NO 2, amino acid 68 of SEQ ID NO 2, amino acids 76–77 of SEQ ID NO 2, amino acid 119 of SEQ ID NO 2, amino acid 143–144 of SEQ ID NO 2, amino acid 161 of SEQ ID NO 2, amino acid 583 of SEQ ID NO 2, amino acid 606 of SEQ ID NO 2, or complements thereof. The polynucleotide can be of any size that is effective to confer specificity to the sequence, e.g., 15 nucleotides (5 amino acids), 24 nucleotides (8 amino acids), 30 nucleotides (10 amino acids), 45 nucleotides (15 amino acids), etc. It can also comprise much longer sequences, e.g., a polynucleotide coding for amino acids 1–263 of SEQ ID NO 2 or 459–614 of SEQ ID NO 2, or a complement thereof.

The present invention also relates genomic DNA from which the polynucleotides of the present invention can be derived. A genomic DNA coding for a human, mouse, or other mammalian polynucleotide, can be obtained routinely, for example, by screening a genomic library (e.g., a YAC library) with a polynucleotide of the present invention, or by searching nucleotide databases, such as GenBank and EMBL, for matches. Promoter and other regulatory regions (including both 5' and 3' regions) can be identified upstream or downstream of coding and expressed RNAs, and assayed routinely for activity, e.g., by joining to a reporter gene (e.g., CAT, GFP, alkaline phosphatase, luciferase, galatosidase). 3'-untranslated sequences (as well as introns) can be used, e.g., to stabilize transcripts, to target transcripts, etc.

Constructs

A polynucleotide of the present invention can comprise additional polynucleotide sequences, e.g., sequences to enhance expression, detection, uptake, cataloging, tagging, etc. A polynucleotide can include only coding sequence; a coding sequence and additional non-naturally occurring or heterologous coding sequence (e.g., sequences coding for leader, signal, secretory, targeting, enzymatic, fluorescent, antibiotic resistance, and other functional or diagnostic peptides); coding sequences and non-coding sequences, e.g., untranslated sequences at either a 5' or 3' end, or dispersed in the coding sequence, e.g., introns.

A polynucleotide according to the present invention also can comprise an expression control sequence operably linked to a polynucleotide as described above. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Promega have been designed to permit a molecule to be inserted into all three reading frames to identify the one that results in polypeptide expression). Expression control sequences can be heterologous or endogenous to the normal gene.

A polynucleotide of the present invention can also comprise nucleic acid vector sequences, e.g., for cloning, expression, amplification, selection, etc. Any effective vector can be used. A vector is, e.g., a polynucleotide molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR54 0, pRIT5 (Pharmacia). Eukaryotic: PWLNEO, pSV2CAT, pOG44, pXT1, pSG (Stratagene), pSVK3, PBPV, PMSG, pSVL (Pharmacia), pCR2.1/TOPO, pCRII/TOPO, pCR4/TOPO, pTrcHisB, pCMV6-XL4, etc. However, any other vector, e.g., plasmids, viruses, or parts thereof, may be used as long as they are replicable and viable in the desired host. The vector can also comprise sequences which enable it to replicate in the host whose genome is to be modified.

Hybridization

Polynucleotide hybridization, as discussed in more detail below, is useful in a variety of applications, including, in gene detection methods, for identifying mutations, for making mutations, to identify homologs in the same and different species, to identify related members of the same gene family, in diagnostic and prognostic assays, in therapeutic applications (e.g., where an antisense polynucleotide is used to inhibit expression), etc.

The ability of two single-stranded polynucleotide preparations to hybridize together is a measure of their nucleotide sequence complementarity, e.g., base-pairing between nucleotides, such as A–T, G–C, etc. The invention thus also relates to polynucleotides, and their complements, which hybridize to a polynucleotide comprising a nucleotide sequence as set forth in SEQ ID NO 1 and genomic sequences thereof. A nucleotide sequence hybridizing to the latter sequence will have a complementary polynucleotide strand, or act as a template for one in the presence of a polymerase (i.e., an appropriate polynucleotide synthesizing enzyme). The present invention includes both strands of polynucleotide, e.g., a sense strand and an anti-sense strand.

Hybridization conditions can be chosen to select polynucleotides which have a desired amount of nucleotide complementarity with the nucleotide sequences set forth in SEQ ID NO 1 and genomic sequences thereof. A polynucleotide capable of hybridizing to such sequence, preferably, possesses, e.g., about 70%, 75%, 80%, 85%, 87%, 90%, 92%, 95%, 97%, 99%, or 100% complementarity, between the sequences. The present invention particularly relates to polynucleotide sequences which hybridize to the nucleotide sequences set forth in SEQ ID NO 1 or genomic sequences thereof, under low or high stringency conditions. These conditions can be used, e.g., to select corresponding homologs in non-human species.

Polynucleotides which hybridize to polynucleotides of the present invention can be selected in various ways. Filter-type blots (i.e., matrices containing polynucleotide, such as nitrocellulose), glass chips, and other matrices and substrates comprising polynucleotides (short or long) of interest, can be incubated in a prehybridization solution (e.g., 6×SSC, 0.5% SDS, 100 μg/ml denatured salmon sperm DNA, 5× Denhardt's solution, and 50% formamide), at 22–68° C., overnight, and then hybridized with a detectable polynucleotide probe under conditions appropriate to achieve the desired stringency. In general, when high homology or sequence identity is desired, a high temperature can be used (e.g., 65° C.). As the homology drops, lower washing temperatures are used. For salt concentrations, the lower the salt concentration, the higher the stringency. The length of the probe is another consideration. Very short probes (e.g., less than 100 base pairs) are washed at lower temperatures, even if the homology is high. With short probes, formamide can be omitted. See, e.g., *Current Protocols in Molecular Biology*, Chapter 6, Screening of Recombinant Libraries; Sambrook et al., *Molecular Cloning*, 1989, Chapter 9.

For instance, high stringency conditions can be achieved by incubating the blot overnight (e.g., at least 12 hours) with a long polynucleotide probe in a hybridization solution containing, e.g., about 5×SSC, 0.5% SDS, 100 µg/ml denatured salmon sperm DNA and 50% formamide, at 42° C. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity.

Other non-limiting examples of high stringency conditions includes a final wash at 65° C. in aqueous buffer containing 30 mM NaCl and 0.5% SDS. Another example of high stringent conditions is hybridization in 7% SDS, 0.5 M NaPO$_4$, pH 7, 1 mM EDTA at 50° C., e.g., overnight, followed by one or more washes with a 1% SDS solution at 42° C. Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time.

Hybridization can also be based on a calculation of melting temperature (Tm) of the hybrid formed between the probe and its target, as described in Sambrook et al. Generally, the temperature Tm at which a short oligonucleotide (containing 18 nucleotides or fewer) will melt from its target sequence is given by the following equation: Tm=(number of A's and T's)×2° C.+(number of C's and G's)×4° C. For longer molecules, Tm=81.5+16.6 log$_{10}$[Na$^+$]+0.41(% GC)−600/N where [Na$^+$] is the molar concentration of sodium ions, % GC is the percentage of GC base pairs in the probe, and N is the length. Hybridization can be carried out at several degrees below this temperature to ensure that the probe and target can hybridize. Mismatches can be allowed for by lowering the temperature even further.

Stringent conditions can be selected to isolate sequences, and their complements, which have, e.g., at least about 90%, 95%, or 97%, nucleotide complementarity between the probe (e.g., a short polynucleotide of SEQ ID NO 1 or genomic sequences thereof) and a target polynucleotide.

Other homologs of polynucleotides of the present invention can be obtained from mammalian and non-mammalian sources according to various methods. For example, hybridization with a polynucleotide can be employed to select homologs, e.g., as described in Sambrook et al., *Molecular Cloning*, Chapter 11, 1989. Such homologs can have varying amounts of nucleotide and amino acid sequence identity and similarity to such polynucleotides of the present invention. Mammalian organisms include, e.g., mice, rats, monkeys, pigs, cows, etc. Non-mammalian organisms include, e.g., vertebrates, invertebrates, zebra fish, chicken, *Drosophila*, *C. elegans*, Xenopus, yeast such as *S. pombe*, *S. cerevisiae*, roundworms, prokaryotes, plants, *Arabidopsis*, artemia, viruses, etc.

Alignment

Alignments can be accomplished by using any effective algorithm. For pairwise alignments of DNA sequences, the methods described by Wilbur-Lipman (e.g., Wilbur and Lipman, *Proc. Natl. Acad. Sci.*, 80:726–730, 1983) or Martinez/Needleman-Wunsch (e.g., Martinez, *Nucleic Acid Res.*, 11:4629–4634, 1983) can be used. For instance, if the Martinez/Needleman-Wunsch DNA alignment is applied, the minimum match can be set at 9, gap penalty at 1.10, and gap length penalty at 0.33. The results can be calculated as a similarity index, equal to the sum of the matching residues divided by the sum of all residues and gap characters, and then multiplied by 100 to express as a percent. Similarity index for related genes at the nucleotide level in accordance with the present invention can be greater than 70%, 80%, 85%, 90%, 95%, 99%, or more. Pairs of protein sequences can be aligned by the Lipman-Pearson method (e.g., Lipman and Pearson, *Science*, 227:1435–1441, 1985) with k-tuple set at 2, gap penalty set at 4, and gap length penalty set at 12. Results can be expressed as percent similarity index, where related genes at the amino acid level in accordance with the present invention can be greater than 65%, 70%, 75%, 80%, 85%, 90%, 95%, 99%, or more. Various commercial and free sources of alignment programs are available, e.g., MegAlign by DNA Star, BLAST (National Center for Biotechnology Information), BCM (Baylor College of Medicine) Launcher, etc. BLAST can be used to calculate amino acid sequence identity, amino acid sequence homology, and nucleotide sequence identity. These calculations are made along the entire length of each of the target sequences which are to be compared.

Percent sequence identity can also be determined by other conventional methods, e.g., as described in Altschul et al., *Bull. Math. Bio.* 48: 603–616, 1986 and Henikoff and Henikoff, *Proc. Natl. Acad. Sci. USA* 89:10915–10919, 1992.

Specific Polynucleotide Probes

A polynucleotide of the present invention can comprise any continuous nucleotide sequence of SEQ ID NO 1, sequences which share sequence identity thereto, or complements thereof. The term "probe" refers to any substance that can be used to detect, identify, isolate, etc., another substance. A polynucleotide probe is comprised of nucleic acid can be used to detect, identify, etc., other nucleic acids, such as DNA and RNA.

These polynucleotides can be of any desired size that is effective to achieve the specificity desired. For example, a probe can be from about 7 or 8 nucleotides to several thousand nucleotides, depending upon its use and purpose. For instance, a probe used as a primer PCR can be shorter than a probe used in an ordered array of polynucleotide probes. Probe sizes vary, and the invention is not limited in any way by their size, e.g., probes can be from about 7–2000 nucleotides, 7–1000, 8–700, 8–600, 8–500, 8–400, 8–300, 8–150, 8–100, 8–75, 7–50, 10–25, 14–16, at least about 8, at least about 10, at least about 15, at least about 25, etc. The polynucleotides can have non-naturally-occurring nucleotides, e.g., inosine, AZT, 3TC, etc. The polynucleotides can have 100% sequence identity or complementarity to a sequence of SEQ ID NO 1, or it can have mismatches or nucleotide substitutions, e.g., 1, 2, 3, 4, or 5 substitutions. The probes can be single-stranded or double-stranded.

In accordance with the present invention, a polynucleotide can be present in a kit, where the kit includes, e.g., one or more polynucleotides, a desired buffer (e.g., phosphate, tris, etc.), detection compositions, RNA or cDNA from different tissues to be used as controls, libraries, etc. The polynucleotide can be labeled or unlabeled, with radioactive or non-radioactive labels as known in the art. Kits can comprise one or more pairs of polynucleotides for amplifying nucleic acids specific for Urb-ctf, e.g., comprising a forward and reverse primer effective in PCR. These include both sense and anti-sense orientations. For instance, in PCR-based methods (such as RT-PCR), a pair of primers are typically used, one having a sense sequence and the other having an antisense sequence.

Another aspect of the present invention is a nucleotide sequence that is specific to, or for, a selective polynucleotide. The phrases "specific for" or "specific to" a polynucleotide have a functional meaning that the polynucleotide can be used to identify the presence of one or more target genes in a sample and distinguish them from non-target genes. It is specific in the sense that it can be used to detect polynucleotides above background noise ("non-specific binding"). A specific sequence is a defined order of nucleotides (or amino acids, if it is polypeptide sequence) which occurs in the polynucleotide, e.g., in the nucleotide sequences of SEQ ID NO 1, and which is characteristic of that target sequence, and substantially no non-target sequences. A probe or mixture of probes can comprise a sequence or sequences that are specific to a plurality of target sequences, e.g., where the sequence is a consensus sequence, a functional domain, etc., e.g., capable of recognizing a family of related genes. Such sequences can be used as probes in any of the methods described herein or incorporated by reference. Both sense and antisense nucleotide sequences are included. A specific polynucleotide according to the present invention can be determined routinely.

A polynucleotide comprising a specific sequence can be used as a hybridization probe to identify the presence of, e.g., human or mouse polynucleotide, in a sample comprising a mixture of polynucleotides, e.g., on a Northern blot. Hybridization can be performed under high stringent conditions (see, above) to select polynucleotides (and their complements which can contain the coding sequence) having at least 90%, 95%, 99%, etc., identity (i.e., complementarity) to the probe, but less stringent conditions can also be used. A specific polynucleotide sequence can also be fused in-frame, at either its 5' or 3' end, to various nucleotide sequences as mentioned throughout the patent, including coding sequences for enzymes, detectable markers, GFP, etc, expression control sequences, etc.

A polynucleotide probe, especially one that is specific to a polynucleotide of the present invention, can be used in gene detection and hybridization methods as already described. In one embodiment, a specific polynucleotide probe can be used to detect whether a particular tissue or cell-type is present in a target sample. To carry out such a method, a selective polynucleotide can be chosen which is characteristic of the desired target tissue. Such polynucleotide is preferably chosen so that it is expressed or displayed in the target tissue, but not in other tissues which are present in the sample. For instance, if detection of is desired, it may not matter whether the selective polynucleotide is expressed in other tissues, as long as it is not expressed in cells normally present in blood, e.g., peripheral blood mononuclear cells. Starting from the selective polynucleotide, a specific polynucleotide probe can be designed which hybridizes (if hybridization is the basis of the assay) under the hybridization conditions to the selective polynucleotide, whereby the presence of the selective polynucleotide can be determined.

Probes which are specific for polynucleotides of the present invention can also be prepared using involve transcription-based systems, e.g., incorporating an RNA polymerase promoter into a selective polynucleotide of the present invention, and then transcribing anti-sense RNA using the polynucleotide as a template. See, e.g., U.S. Pat. No. 5,545,522.

Polynucleotide Composition

A polynucleotide according to the present invention can comprise, e.g., DNA, RNA, synthetic polynucleotide, peptide polynucleotide, modified nucleotides, dsDNA, ssDNA, ssRNA, dsRNA, and mixtures thereof. A polynucleotide can be single- or double-stranded, triplex, DNA:RNA, duplexes, comprise hairpins, and other secondary structures, etc. Nucleotides comprising a polynucleotide can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAse H, improved in vivo stability, etc. See, e.g., U.S. Pat. No. 5,378,825. Any desired nucleotide or nucleotide analog can be incorporated, e.g., 6-mercaptoguanine, 8-oxo-guanine, etc.

Various modifications can be made to the polynucleotides, such as attaching detectable markers (avidin, biotin, radioactive elements, fluorescent tags and dyes, energy transfer labels, energy-emitting labels, binding partners, etc.) or moieties which improve hybridization, detection, and/or stability. The polynucleotides can also be attached to solid supports, e.g., nitrocellulose, magnetic or paramagnetic microspheres (e.g., as described in U.S. Pat. No. 5,411,863; U.S. Pat. No. 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967, 5,476,925, and 5,478,893.

Polynucleotide according to the present invention can be labeled according to any desired method. The polynucleotide can be labeled using radioactive tracers such as $^{32}P$, $^{35}S$, $^{3}H$, or $^{14}C$, to mention some commonly used tracers. The radioactive labeling can be carried out according to any method, such as, for example, terminal labeling at the 3' or 5' end using a radiolabeled nucleotide, polynucleotide kinase (with or without dephosphorylation with a phosphatase) or a ligase (depending on the end to be labeled). A non-radioactive labeling can also be used, combining a polynucleotide of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

Nucleic Acid Detection Methods

Another aspect of the present invention relates to methods and processes for detecting Urb-ctf. Detection methods have a variety of applications, including for diagnostic, prognostic, forensic, and research applications. To accomplish gene detection, a polynucleotide in accordance with the present invention can be used as a "probe." The term "probe" or "polynucleotide probe" has its customary meaning in the art, e.g., a polynucleotide which is effective to identify (e.g., by hybridization), when used in an appropriate process, the presence of a target polynucleotide to which it is designed. Identification can involve simply determining presence or absence, or it can be quantitative, e.g., in assessing amounts of a gene or gene transcript present in a sample. Probes can be useful in a variety of ways, such as for diagnostic purposes, to identify homologs, and to detect, quantitate, or isolate a polynucleotide of the present invention in a test sample.

Assays can be utilized which permit quantification and/or presence/absence detection of a target nucleic acid in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., Science, 241:53, 1988; U.S. Pat. Nos. 4,683,195, 4,683,202, and 6,040,166; PCR Protocols: A Guide to Methods and Applications, Innis et al., eds., Academic Press, New York, 1990), reverse transcriptase polymerase chain reaction ("RT-PCR"), anchored PCR, rapid amplification of cDNA ends ("RACE") (e.g., Schaefer in Gene Cloning and Analysis: Current Innovations, Pages 99–115, 1997), ligase chain reaction ("LCR") (EP 320 308), one-sided PCR (Ohara et al., Proc. Natl. Acad. Sci., 86:5673–5677, 1989), indexing methods (e.g., U.S. Pat. No. 5,508,169), in situ hybridization, differential display (e.g., Liang et al., Nucl. Acid. Res., 21:3269–3275, 1993; U.S. Pat. Nos. 5,262,311, 5,599,672 and 5,965,409; WO97/18454; Prashar and Weissman, Proc. Natl. Acad. Sci., 93:659–663, and U.S. Pat. Nos. 6,010,850 and 5,712,126; Welsh et al., Nucleic Acid Res., 20:4965–4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan™, etc. Additional useful methods include, but are not limited to, e.g., template-based amplification methods, competitive PCR (e.g., U.S. Pat. No. 5,747,251), redox-based assays (e.g., U.S. Pat. No. 5,871,918), Taqman-based assays (e.g., Holland et al., Proc. Natl. Acad, Sci., 88:7276–7280, 1991; U.S. Pat. Nos. 5,210,015 and 5,994,063), real-time fluorescence-based monitoring (e.g., U.S. Pat. No. 5,928,907), molecular energy transfer labels (e.g., U.S. Pat. Nos. 5,348,853, 5,532,129, 5,565,322, 6,030,787, and 6,117,635; Tyagi and Kramer, Nature Biotech., 14:303–309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., Methods Mol. & Cell. Biol. 2, 17–25, 1990; Eberwine et al., 1992, Proc. Natl. Acad. Sci., 89, 3010–3014, 1992; U.S. Pat. No. 5,723,290). These and other methods can be carried out conventionally, e.g., as described in the mentioned publications.

Many of such methods may require that the polynucleotide is labeled, or comprises a particular nucleotide type useful for detection. The present invention includes such modified polynucleotides that are necessary to carry out such methods. Thus, polynucleotides can be DNA, RNA, DNA:RNA hybrids, PNA, etc., and can comprise any modification or substituent which is effective to achieve detection.

Detection can be desirable for a variety of different purposes, including research, diagnostic, prognostic, and forensic. For diagnostic purposes, it may be desirable to identify the presence or quantity of a polynucleotide sequence in a sample, where the sample is obtained from tissue, cells, body fluids, etc. In a preferred method as described in more detail below, the present invention relates to a method of detecting a polynucleotide comprising, contacting a target polynucleotide in a test sample with a polynucleotide probe under conditions effective to achieve hybridization between the target and probe; and detecting hybridization.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Detection can be accomplished in combination with polynucleotide probes for other genes, e.g., genes which are expressed in other disease states, tissues, cells, such as brain, heart, kidney, spleen, thymus, liver, stomach, small intestine, colon, muscle, lung, testis, placenta, pituitary, thyroid, skin, adrenal gland, pancreas, salivary gland, uterus, ovary, prostate gland, peripheral blood cells (T-cells, lymphocytes, etc.), embryo, normal breast fat, adult and embryonic stem cells, specific cell-types, such as endothelial, epithelial, myocytes, adipose, luminal epithelial, basoepithelial, myoepithelial, stromal cells, etc.

Polynucleotides can be used in wide range of methods and compositions, including for detecting, diagnosing, staging, grading, assessing, prognosticating, etc. diseases and disorders associated with Urb-ctf, for monitoring or assessing therapeutic and/or preventative measures, in ordered arrays, etc. Any method of detecting genes and polynucleotides of SEQ ID NO 1 can be used; certainly, the present invention is not to be limited how such methods are implemented.

Along these lines, the present invention relates to methods of detecting Urb-ctf in a sample comprising nucleic acid. Such methods can comprise one or more the following steps in any effective order, e.g., contacting said sample with a polynucleotide probe under conditions effective for said probe to hybridize specifically to nucleic acid in said sample, and detecting the presence or absence of probe hybridized to nucleic acid in said sample, wherein said probe is a polynucleotide which is SEQ ID NO 1, a polynucleotide having, e.g., about 70%, 80%, 85%, 90%, 95%, 99%, or more sequence identity thereto, effective or specific fragments thereof, or complements thereto. The detection method can be applied to any sample, e.g., cultured primary, secondary, or established cell lines, tissue biopsy, blood, urine, stool, cerebral spinal fluid, and other bodily fluids, for any purpose.

Contacting the sample with probe can be carried out by any effective means in any effective environment. It can be accomplished in a solid, liquid, frozen, gaseous, amorphous, solidified, coagulated, colloid, etc., mixtures thereof, matrix. For instance, a probe in an aqueous medium can be contacted with a sample which is also in an aqueous medium, or which is affixed to a solid matrix, or vice-versa.

Generally, as used throughout the specification, the term "effective conditions" means, e.g., the particular milieu in which the desired effect is achieved. Such a milieu, includes, e.g., appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including substrate, oxygen, carbon dioxide, etc.). When hybridization is the chosen means of achieving detection, the probe and sample can be combined such that the resulting conditions are functional for said probe to hybridize specifically to nucleic acid in said sample.

The phrase "hybridize specifically" indicates that the hybridization between single-stranded polynucleotides is based on nucleotide sequence complementarity. The effective conditions are selected such that the probe hybridizes to a preselected and/or definite target nucleic acid in the sample. For instance, if detection of a polynucleotide set forth in SEQ ID NO 1 is desired, a probe can be selected which can hybridize to such target gene under high stringent conditions, without significant hybridization to other genes in the sample. To detect homologs of a polynucleotide set forth in SEQ ID NO 1, the effective hybridization conditions can be less stringent, and/or the probe can comprise codon degeneracy, such that a homolog is detected in the sample.

As already mentioned, the methods can be carried out by any effective process, e.g., by Northern blot analysis, polymerase chain reaction (PCR), reverse transcriptase PCR, RACE PCR, in situ hybridization, etc., as indicated above. When PCR based techniques are used, two or more probes are generally used. One probe can be specific for a defined sequence which is characteristic of a selective polynucleotide, but the other probe can be specific for the selective polynucleotide, or specific for a more general sequence, e.g., a sequence such as polyA which is characteristic of mRNA, a sequence which is specific for a promoter, ribosome binding site, or other transcriptional features, a consensus sequence (e.g., representing a functional domain). For the former aspects, 5' and 3' probes (e.g., polyA, Kozak, etc.) are preferred which are capable of specifically hybridizing to the ends of transcripts. When PCR is utilized, the probes can also be referred to as "primers" in that they can prime a DNA polymerase reaction.

In addition to testing for the presence or absence of polynucleotides, the present invention also relates to determining the amounts at which polynucleotides of the present invention are expressed in sample and determining the differential expression of such polynucleotides in samples. Such methods can involve substantially the same steps as described above for presence/absence detection, e.g., contacting with probe, hybridizing, and detecting hybridized probe, but using more quantitative methods and/or comparisons to standards.

The amount of hybridization between the probe and target can be determined by any suitable methods, e.g., PCR, RT-PCR, RACE PCR, Northern blot, polynucleotide microarrays, Rapid-Scan, etc., and includes both quantitative and qualitative measurements. For further details, see the hybridization methods described above and below. Determining by such hybridization whether the target is differentially expressed (e.g., up-regulated or down-regulated) in the sample can also be accomplished by any effective means. For instance, the target's expression pattern in the sample can be compared to its pattern in a known standard, such as in a normal tissue, or it can be compared to another gene in the same sample. When a second sample is utilized for the comparison, it can be a sample of normal tissue that is known not to contain diseased cells. The comparison can be performed on samples which contain the same amount of RNA (such as polyadenylated RNA or total RNA), or, on RNA extracted from the same amounts of starting tissue. Such a second sample can also be referred to as a control or standard. Hybridization can also be compared to a second target in the same tissue sample. Experiments can be performed that determine a ratio between the target nucleic acid and a second nucleic acid (a standard or control), e.g., in a normal tissue. When the ratio between the target and control are substantially the same in a normal and sample, the sample is determined or diagnosed not to contain cells. However, if the ratio is different between the normal and sample tissues, the sample is determined to contain cancer cells. The approaches can be combined, and one or more second samples, or second targets can be used. Any second target nucleic acid can be used as a comparison, including "housekeeping" genes, such as beta-actin, alcohol dehydrogenase, or any other gene whose expression does not vary depending upon the disease status of the cell.

Methods of Identifying Polymorphisms, Mutations, etc., of Urb-ctf

Polynucleotides of the present invention can also be utilized to identify mutant alleles, SNPs, gene rearrangements and modifications, and other polymorphisms of the wild-type gene. Mutant alleles, polymorphisms, SNPs, etc., can be identified and isolated from cancers that are known, or suspected to have, a genetic component. Identification of such genes can be carried out routinely (see, above for more guidance), e.g., using PCR, hybridization techniques, direct sequencing, mismatch reactions (see, e.g., above), RFLP analysis, SSCP (e.g., Orita et al., *Proc. Natl. Acad. Sci.,* 86:2766, 1992), etc., where a polynucleotide having a sequence selected from SEQ ID NO 1 is used as a probe. The selected mutant alleles, SNPs, polymorphisms, etc., can be used diagnostically to determine whether a subject has, or is susceptible to a disorder associated with Urb-ctf, as well as to design therapies and predict the outcome of the disorder. Methods involve, e.g., diagnosing a disorder associated with Urb-ctf or determining susceptibility to a disorder, comprising, detecting the presence of a mutation in a gene represented by a polynucleotide selected from SEQ ID NO 1. The detecting can be carried out by any effective method, e.g., obtaining cells from a subject, determining the gene sequence or structure of a target gene (using, e.g., mRNA, cDNA, genomic DNA, etc), comparing the sequence or structure of the target gene to the structure of the normal gene, whereby a difference in sequence or structure indicates a mutation in the gene in the subject. Polynucleotides can also be used to test for mutations, SNPs, polymorphisms, etc., e.g., using mismatch DNA repair technology as described in U.S. Pat. No. 5,683,877; U.S. Pat. No. 5,656,430; Wu et al., *Proc. Natl. Acad. Sci.,* 89:8779–8783, 1992.

The present invention also relates to methods of detecting polymorphisms in Urb-ctf, comprising, e.g., comparing the structure of: genomic DNA comprising all or part of Urb-ctf, mRNA comprising all or part of Urb-ctf, cDNA comprising all or part of Urb-ctf, or a polypeptide comprising all or part of Urb-ctf, with the structure of Urb-ctf set forth in SEQ ID NO 1. The methods can be carried out on a sample from any source, e.g., cells, tissues, body fluids, blood, urine, stool, hair, egg, sperm, cerebral spinal fluid, etc.

These methods can be implemented in many different ways. For example, "comparing the structure" steps include, but are not limited to, comparing restriction maps, nucleotide sequences, amino acid sequences, RFLPs, Dnase sites, DNA methylation fingerprints (e.g., U.S. Pat. No. 6,214,556), protein cleavage sites, molecular weights, electrophoretic mobilities, charges, ion mobility, etc., between a standard Urb-ctf and a test Urb-ctf. The term "structure" can refer to any physical characteristics or configurations which can be used to distinguish between nucleic acids and polypeptides. The methods and instruments used to accomplish the comparing step depends upon the physical characteristics which are to be compared. Thus, various techniques are contemplated, including, e.g., sequencing machines (both amino acid and polynucleotide), electrophoresis, mass spectrometer (U.S. Pat. Nos. 6,093,541, 6,002,127), liquid chromatography, HPLC, etc.

To carry out such methods, "all or part" of the gene or polypeptide can be compared. For example, if nucleotide sequencing is utilized, the entire gene can be sequenced, including promoter, introns, and exons, or only parts of it can be sequenced and compared, e.g., exon 1, exon 2, etc.

Mutagenesis

Mutated polynucleotide sequences of the present invention are useful for various purposes, e.g., to create mutations of the polypeptides they encode, to identify functional regions of genomic DNA, to produce probes for screening libraries, etc. Mutagenesis can be carried out routinely according to any effective method, e.g., oligonucleotide-directed (Smith, M., *Ann. Rev. Genet.* 19:423–463, 1985), degenerate oligonucleotide-directed (Hill et al., *Method Enzymology*, 155:558–568, 1987), region-specific (Myers et al., *Science,* 229:242–246, 1985; Derbyshire et al., *Gene,* 46:145, 1986; Ner et al., *DNA,* 7:127, 1988), linker-scanning (McKnight and Kingsbury, *Science,* 217:316–324, 1982), directed using PCR, recursive ensemble mutagenesis (Arkin and Yourvan, *Proc. Natl. Acad. Sci.,* 89:7811–7815, 1992), random mutagenesis (e.g., U.S. Pat. Nos. 5,096,815; 5,198, 346; and 5,223,409), site-directed mutagenesis (e.g., Walder et al., *Gene,* 42:133, 1986; Bauer et al., *Gene,* 37:73, 1985; Craik, *Bio Techniques*, Jan. 1985, 12–19; Smith et al., *Genetic Engineering: Principles and Methods*, Plenum Press, 1981), phage display (e.g., Lowman et al., *Biochem.* 30:10832–10837, 1991; Ladner et al., U.S. Pat. No. 5,223, 409; Huse, WIPO Publication WO 92/06204), etc. Desired sequences can also be produced by the assembly of target sequences using mutually priming oligonucleotides (Uhlmann, *Gene,* 71:29–40, 1988). For directed mutagenesis methods, analysis of the three-dimensional structure of the Urb-ctf polypeptide can be used to guide and facilitate making mutants which effect polypeptide activity. Sites of substrate-enzyme interaction or other biological activities can also be determined by analysis of crystal structure as determined by such techniques as nuclear magnetic resonance, crystallography or photoaffinity labeling. See, for example, de Vos et al., Science 255:306–312, 1992; Smith et al., J. Mol. Biol. 224:899–904, 1992; Wlodaver et al., FEBS Lett. 309:59–64, 1992.

In addition, libraries of Urb-ctf and fragments thereof can be used for screening and selection of Urb-ctf variants. For instance, a library of coding sequences can be generated by treating a double-stranded DNA with a nuclease under conditions where the nicking occurs, e.g., only once per molecule, denaturing the double-stranded DNA, renaturing it to for double-stranded DNA that can include sense/antisense pairs from different nicked products, removing single-stranded portions from reformed duplexes by treatment with S1 nuclease, and ligating the resulting DNAs into an expression vecore. By this method, xpression libraries can be made comprising "mutagenized" Urb-ctf. The entire coding sequence or parts thereof can be used.

Polynucleotide Expression, Polypeptides Produced thereby, and Specific-binding Partners thereto A polynucleotide according to the present invention can be expressed in a variety of different systems, in vitro and in vivo, according to the desired purpose. For example, a polynucleotide can be inserted into an expression vector, introduced into a desired host, and cultured under conditions effective to achieve expression of a polypeptide coded for by the polynucleotide, to search for specific binding partners. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding polynucleotide is adjacent to a dhfr gene), cycloheximide, cell densities, culture dishes, etc. A polynucleotide can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a polynucleotide of the present invention has been introduced is a transformed host cell. The polynucleotide can be extrachromosomal or integrated into a chromosome(s) of the host cell. It can be stable or transient. An expression vector is selected for its compatibility with the host cell. Host cells include, mammalian cells, e.g., COS, CV1, BHK, CHO, HeLa, LTK, NIH 3T3, ZR-75-1 (ATCC CRL-1500), ZR-75-30 (ATCC CRL-1504), UACC-812 (ATCC CRL-1897), UACC-893 (ATCC CRL-1902), HCC38 (ATCC CRL-2314), HCC70 (CRL-2315), and other HCC cell lines (e.g., as deposited with the ATCC), AU565 (ATCC CRL-2351), Hs 496.T (ATCC CRL-7303), Hs 748.T (ATCC CRL-7486), SW527 (ATCC CRL-7940), 184A1 (ATCC CRL-8798), MCF cell lines (e.g., 10A and others deposited with the ATCC), MDA-MB-134-VI (ATCC HTB-23 and other MDA cell lines), SK-BR-3 (ATCC HTB-30), ME-180 (ATCC HTB-33), Hs 578Bst (ATCC HTB-125), Hs 578T (ATCC HTB-126), T-47D (ATCC HTB-133), insect cells, such as Sf9 (*S. frugipeda*) and *Drosophila*, bacteria, such as *E. coli, Streptococcus, bacillus,* yeast, such as Sacharomyces, *S. cerevisiae,* fungal cells, plant cells, embryonic or adult stem cells (e.g., mammalian, such as mouse or human).

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, MMTV, SV40, trp, lac, tac, or T7 promoters for bacterial hosts; or alpha factor, alcohol oxidase, or PGH promoters for yeast. RNA promoters can be used to produced RNA transcripts, such as T7 or SP6. See, e.g., Melton et al., *Polynucleotide Res.,* 12(18):7035–7056, 1984; Dunn and Studier. *J. Mol. Bio.,* 166:477–435, 1984; U.S. Pat. No. 5,891,636; Studier et al., *Gene Expression Technology, Methods in Enzymology,* 85:60–89, 1987. In addition, as discussed above, translational signals (including in-frame insertions) can be included.

When a polynucleotide is expressed as a heterologous gene in a transfected cell line, the gene is introduced into a cell as described above, under effective conditions in which the gene is expressed. The term "heterologous" means that the gene has been introduced into the cell line by the "hand-of-man." Introduction of a gene into a cell line is discussed above. The transfected (or transformed) cell expressing the gene can be lysed or the cell line can be used intact.

For expression and other purposes, a polynucleotide can contain codons found in a naturally-occurring gene, transcript, or cDNA, for example, e.g., as set forth in SEQ ID NO 1, or it can contain degenerate codons coding for the same amino acid sequences. For instance, it may be desirable to change the codons in the sequence to optimize the sequence for expression in a desired host. See, e.g., U.S. Pat. Nos. 5,567,600 and 5,567,862.

A polypeptide according to the present invention can be recovered from natural sources, transformed host cells (culture medium or cells) according to the usual methods, including, detergent extraction (e.g., non-ionic detergent, Triton X-100, CHAPS, octylglucoside, Igepal CA-630), ammonium sulfate or ethanol precipitation, acid extraction, anion or cation exchange chromatography, phosphocellulose chromatography, hydrophobic interaction chromatography, hydroxyapatite chromatography, lectin chromatography, gel electrophoresis. Protein refolding steps can be used, as necessary, in completing the configuration of the mature protein. Finally, high performance liquid chromatography (HPLC) can be employed for purification steps. Another approach is express the polypeptide recombinantly with an affinity tag (Flag epitope, HA epitope, myc epitope, 6xHis, maltose binding protein, chitinase, etc) and then purify by anti-tag antibody-conjugated affinity chromatography.

The present invention also relates to polypeptides of Urb-ctf, e.g., an isolated human Urb-ctf polypeptide comprising or having the amino acid sequence set forth in SEQ ID NO 2, an isolated human Urb-ctf polypeptide comprising an amino acid sequence having 99% or more sequence identity to the amino acid sequence set forth in SEQ ID NO 2, and have having one or more of Urb-ctf activities, such as transcriptional regulatory activity, DNA-binding activity, dimerization activity, immunological activity, etc. Fragments specific to Urb-ctf can also used, e.g., to produce antibodies or other immune responses, as competitors to DNA-binding, dimerization, or transcriptional activity, etc. These fragments can be referred to as being "specific for" Urb-ctf. The latter phrase, as already defined, indicates that the peptides are characteristic of Urb-ctf, and the defined sequences are substantially absent from all other protein types. Such polypeptides can be of any size which is necessary to confer specificity, e.g., 5, 8, 10, 12, 15, 20, etc. Especially preferred are polypeptides which comprise the following amino acid residues, e.g., amino acid 38 of SEQ ID NO 2, amino acid 68 of SEQ ID NO 2, amino acids 76–77 of SEQ ID NO 2, amino acid 119 of SEQ ID NO 2, amino acid 143–144 of SEQ ID NO 2, amino acid 161 of SEQ ID NO 2, amino acid 583 of SEQ ID NO 2, or amino acid 606 of SEQ ID NO 2, including peptides having amino acids 1–263 of SEQ ID NO 2 or 459–614 of SEQ ID NO 2.

The present invention also relates to antibodies, and other specific-binding partners, which are specific for polypeptides encoded by polynucleotides of the present invention, e.g., Urb-ctf. Antibodies, e.g., polyclonal, monoclonal, recombinant, chimeric, humanized, single-chain, Fab, and fragments thereof, can be prepared according to any desired method. See, also, screening recombinant immunoglobulin libraries (e.g., Orlandi et al., *Proc. Natl. Acad. Sci.,* 86:3833–3837, 1989; Huse et al., *Science,* 256:1275–1281, 1989); in vitro stimulation of lymphocyte populations; Winter and Milstein, *Nature,* 349: 293–299, 1991. The antibodies can be IgM, IgG, subtypes, IgG2a, IgG1, etc. Antibodies, and immune responses, can also be generated by administering naked DNA See, e.g., U.S. Pat. Nos. 5,703,055; 5,589,466; 5,580,859. Antibodies can be used from any source, including, goat, rabbit, mouse, chicken (e.g., IgY; see, Duan, W0/029444 for methods of making antibodies in avian hosts, and harvesting the antibodies from the eggs). An antibody specific for a polypeptide means that the antibody recognizes a defined sequence of amino acids within or including the polypeptide. Other specific binding partners include, e.g., aptamers and PNA. Antibodies can be prepared against specific epitopes or domains of Urb-ctf, e.g., an antibody which is specific for an epitope comprising, amino acid 38 of SEQ ID NO 2, amino acid 68 of SEQ ID NO 2, amino acids 76–77 of SEQ ID NO 2, amino acid 119 of SEQ ID NO 2, amino acid 143–144 of SEQ ID NO 2, amino acid 161 of SEQ ID NO 2, amino acid 583 of SEQ ID NO 2, amino acid 606 of SEQ ID NO 2, etc. By being specific to an epitope, it means that the antibody recognizes a defined sequence of amino acids which includes the particular amino acid residue.

The preparation of polyclonal antibodies is well-known to those skilled in the art. See, for example, Green et al., Production of Polyclonal Antisera, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992). The preparation of monoclonal antibodies likewise is conventional. See, for example, Kohler & Milstein, Nature 256:495 (1975); Coligan et al., sections 2.5.1–2.6.7; and Harlow et al., ANTIBODIES: A LABORATORY MANUAL, page 726 (Cold Spring Harbor Pub. 1988).

Antibodies can also be humanized, e.g., where they are to be used therapeutically. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989), which is hereby incorporated in its entirety by reference. Techniques for producing humanized monoclonal antibodies are described, for example, in U.S. Pat. No. 6,054,297, Jones et al., Nature 321: 522 (1986); Riechmann et al., Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993).

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12: 433 (1994). Cloning and expression vectors that are useful for producing a human immunoglobulin phage library can be obtained commercially, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described, e.g., in Green et al., Nature Genet. 7:13 (1994); Lonberg et al., Nature 368:856 (1994); and Taylor et al., Int. Immunol. 6:579 (1994).

Antibody fragments of the present invention can be prepared by proteolytic hydrolysis of the antibody or by expression in E. coli of nucleic acid encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and U.S. Pat. No. 4,331,647, and references contained therein. These patents are hereby incorporated in their entireties by reference. See also Nisoiihoff et al., Arch. Biochem. Biophys. 89:230 (1960); Porter, Biochem. J. 73:119 (1959); Edelman et al, METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques can also be used. For example, Fv fragments comprise an association of $V_H$ and $V_L$ chains. This association may be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising nucleic acid sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97(1991); Bird etal.,Science 242:423–426 (1988); Ladneret al., U.S. Pat. No. 4,946,778; Pack et al., Bio/Technology 11: 1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The term "antibody" as used herein includes intact molecules as well as fragments thereof, such as Fab, F(ab')2, and Fv which are capable of binding to an epitopic determinant present in Bin1 polypeptide. Such antibody fragments retain some ability to selectively bind with its antigen or receptor. The term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. Antibodies can be prepared against specific epitopes or polypeptide domains.

Antibodies which bind to Urb-ctf polypeptides of the present invention can be prepared using an intact polypeptide or fragments containing small peptides of interest as the immunizing antigen. For example, it may be desirable to produce antibodies that specifically bind to the N- or C-terminal domains of Urb-ctf. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

Anti-idiotype technology can also be used to produce invention monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Methods of Detecting Polypeptides

Polypeptides coded for by Urb-ctf of the present invention can be detected, visualized, determined, quantitated, etc. according to any effective method. useful methods include, e.g., but are not limited to, immunoassays, RIA (radioimmunassay), ELISA, (enzyme-linked-immunosorbent assay), immunoflourescence, flow cytometry, histology, electron microscopy, light microscopy, in situ assays, immunoprecipitation, Western blot, etc.

Immunoassays may be carried in liquid or on biological support. For instance, a sample (e.g., blood, stool, urine, cells, tissue, cerebral spinal fluid, body fluids, etc.) can be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled Urb-ctf specific antibody. The solid phase support can then be washed with a buffer a second time to remove unbound antibody. The amount of bound label on solid support may then be detected by conventional means.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, polyacrylamides, and magnetite. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads One of the many ways in which gene peptide-specific antibody can be detectably labeled is by linking it to an enzyme and using it in an enzyme immunoassay (EIA). See, e.g., Voller, A., "The Enzyme Linked Immunosorbent Assay (ELISA)," 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla. The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, .alpha.-glycerophosphate, dehydrogenase, triose phosphate isomerase, horseradish peroxidase, alkaline phosphatase, asparaginase, glucose oxidase, beta.-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect Urb-ctf peptides through the use of a radioimmunoassay (RIA). See, e.g., Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as those in the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Diagnostic

The present invention also relates to methods and compositions for diagnosing abreast cancer, or determining susceptibility to it, using polynucleotides, polypeptides, and specific-binding partners of the present invention to detect, assess, determine, etc., Urb-ctf. In such methods, the gene can serve as a marker for the disorder, e.g., where the gene, when mutant, is a direct cause of the disorder; where the gene is affected by another gene(s) which is directly responsible for the disorder, e.g., when the gene is part of the same signaling pathway as the directly responsible gene; and, where the gene is chromosomally linked to the gene(s) directly responsible for the disorder, and segregates with it. Many other situations are possible. To detect, assess, determine, etc., a probe specific for the gene can be employed as described above and below. Any method of detecting and/or assessing the gene can be used, including detecting expression of the gene using polynucleotides, antibodies, or other specific-binding partners.

The present invention relates to methods of diagnosing a disorder associated with Urb-ctf, such as breast cancer, or determining a subject's susceptibility to such disorder, comprising, e.g., assessing the expression of Urb-ctf in a tissue sample comprising tissue or cells suspected of having the disorder (e.g., where the sample comprises breast cancer). The phrase "diagnosing" indicates that it is determined whether the sample has the disorder. A "disorder" means, e.g., any abnormal condition as in a disease or malady. "Determining a subject's susceptibility to a disease or disorder" indicates that the subject is assessed for whether s/he is predisposed to get such a disease or disorder, where the predisposition is indicated by abnormal expression of the gene (e.g., gene mutation, gene expression pattern is not normal, etc.). Predisposition or susceptibility to a disease may result when a such disease is influenced by epigenetic, environmental, etc., factors. This includes prenatal screening where samples from the fetus or embryo (e.g., via amniocentesis or CV sampling) are analyzed for the expression of the gene.

By the phrase "assessing expression of Urb-ctf," it is meant that the functional status of the gene is evaluated. This includes, but is not limited to, measuring expression levels of said gene, determining the genomic structure of said gene, determining the mRNA structure of transcripts from said gene, or measuring the expression levels of polypeptide coded for by said gene. Thus, the term "assessing expression" includes evaluating the all aspects of the transcriptional and translational machinery of the gene. For instance, if a promoter defect causes, or is suspected of causing, the disorder, then a sample can be evaluated (i.e., "assessed") by looking (e.g., sequencing or restriction mapping) at the promoter sequence in the gene, by detecting transcription products (e.g., RNA), by detecting translation product (e.g., polypeptide). Any measure of whether the gene is functional can be used, including, polypeptide, polynucleotide, and functional assays for the gene's biological activity.

In making the assessment, it can be useful to compare the results to a normal gene, e.g., a gene which is not associated with the disorder. The nature of the comparison can be determined routinely, depending upon how the assessing is accomplished. If, for example, the mRNA levels of a sample is detected, then the mRNA levels of a normal can serve as a comparison, or a gene which is known not to be affected by the disorder. Methods of detecting mRNA are well known, and discussed above, e.g., but not limited to, Northern blot analysis, polymerase chain reaction (PCR), reverse transcriptase PCR, RACE PCR, etc. Similarly, if polypeptide production is used to evaluate the gene, then the polypeptide in a normal tissue sample can be used as a comparison, or, polypeptide from a different gene whose expression is known not to be affected by the disorder. These are only examples of how such a method could be carried out.

Assessing the effects of therapeutic and preventative interventions (e.g., administration of a drug, chemotherapy, radiation, etc.) on breast cancer is a major effort in drug discovery, clinical medicine, and pharmacogenomics. The evaluation of therapeutic and preventative measures, whether experimental or already in clinical use, has broad applicability, e.g., in clinical trials, for monitoring the status of a patient, for analyzing and assessing animal models, and in any scenario involving cancer treatment and prevention. Analyzing the expression profiles of polynucleotides of the present invention can be utilized as a parameter by which interventions are judged and measured. Treatment of a disorder can change the expression profile in some manner which is prognostic or indicative of the drug's effect on it. Changes in the profile can indicate, e.g., drug toxicity, return to a normal level, etc. Accordingly, the present invention also relates to methods of monitoring or assessing a therapeutic or preventative measure (e.g., chemotherapy, radiation, anti-neoplastic drugs, antibodies, etc.) in a subject having breast cancer, or, susceptible to such disease, comprising, e.g., detecting the expression levels of Urb-ctf. A subject can be a cell-based assay system, non-human animal model, human patient, etc. Detecting can be accomplished as described for the methods above and below. By "therapeutic or preventative intervention," it is meant, e.g., a drug administered to a patient, surgery, radiation, chemotherapy, and other measures taken to prevent, treat, or diagnose a disorder.

Expression can be assessed in any sample comprising any tissue or cell type, body fluid, etc., as discussed for other methods of the present invention, including cells from breast cancer can be used, or cells derived from breast cancer. By the phrase "cells derived from breast cancer," it is meant that the derived cells originate from breast cancer, e.g., when metastasis from a primary tumor site has occurred, when a progenitor-type or pluripotent cell gives rise to other cells, etc.

Identifying Agent Methods

The present invention also relates to methods of identifying agents, and the agents themselves, which modulate Urb-ctf. These agents can be used to modulate the biological activity of the polypeptide encoded for the gene, or the gene, itself. Agents which regulate the gene or its product are useful in variety of different environments, including as medicinal agents to treat or prevent disorders associated with Urb-ctf and as research reagents to modify the function of tissues and cell.

Methods of identifying agents generally comprise steps in which an agent is placed in contact with the gene, transcription product, translation product, or other target, and then a determination is performed to assess whether the agent "modulates" the target. The specific method utilized will depend upon a number of factors, including, e.g., the target (i.e., is it the gene or polypeptide encoded by it), the environment (e.g., in vitro or in vivo), the composition of the agent, etc.

For modulating the expression of Urb-ctf gene, a method can comprise, in any effective order, one or more of the following steps, e.g., contacting a Urb-ctf gene (e.g., in a cell population) with a test agent under conditions effective for said test agent to modulate the expression of Urb-ctf, and determining whether said test agent modulates said Urb-ctf. An agent can modulate expression of Urb-ctf at any level, including transcription, translation, and/or perdurance of the nucleic acid (e.g., degradation, stability, etc.) in the cell. For modulating the biological activity of Urb-ctf polypeptides, a method can comprise, in any effective order, one or more of the following steps, e.g., contacting a Urb-ctf polypeptide (e.g., in a cell, lysate, or isolated) with a test agent under conditions effective for said test agent to modulate the biological activity of said polypeptide, and determining whether said test agent modulates said biological activity.

Contacting Urb-ctf with the test agent can be accomplished by any suitable method and/or means that places the agent in a position to functionally control expression or biological activity of Urb-ctf present in the sample. Functional control indicates that the agent can exert its physiological effect on Urb-ctf through whatever mechanism it works. The choice of the method and/or means can depend upon the nature of the agent and the condition and type of environment in which the Urb-ctf is presented, e.g., lysate, isolated, or in a cell population (such as, in vivo, in vitro, organ explants, etc.). For instance, if the cell population is an in vitro cell culture, the agent can be contacted with the cells by adding it directly into the culture medium. If the agent cannot dissolve readily in an aqueous medium, it can be incorporated into liposomes, or another lipophilic carrier, and then administered to the cell culture. Contact can also be facilitated by incorporation of agent with carriers and delivery molecules and complexes, by injection, by infusion, etc.

After the agent has been administered in such a way that it can gain access to Urb-ctf, it can be determined whether the test agent modulates Urb-ctf expression or biological activity. Modulation can be of any type, quality, or quantity, e.g., increase, facilitate, enhance, up-regulate, stimulate, activate, amplify, augment, induce, decrease, down-regulate, diminish, lessen, reduce, etc. The modulatory quantity can also encompass any value, e.g., 1%, 5%, 10%, 50%, 75%, 1-fold, 2-fold, 5-fold, 10-fold, 100-fold, etc. To modulate Urb-ctf expression means, e.g., that the test agent has an effect on its expression, e.g., to effect the amount of transcription, to effect RNA splicing, to effect translation of the RNA into polypeptide, to effect RNA or polypeptide stability, to effect polyadenylation or other processing of the RNA, to effect post-transcriptional or post-translational processing, etc. To modulate biological activity means, e.g., that a functional activity of the polypeptide is changed in comparison to its normal activity in the absence of the agent. This effect includes, increase, decrease, block, inhibit, enhance, etc. Biological activities of Urb-ctf include, e.g., transcriptional regulatory activity (e.g., similar to bZIP proteins c-fos and c-jun).

A test agent can be of any molecular composition, e.g., chemical compounds, biomolecules, such as polypeptides, lipids, nucleic acids (e.g., antisense to a polynucleotide sequence selected from SEQ ID NO 1), carbohydrates, antibodies, ribozymes, double-stranded RNA, aptamers, etc. For example, polypeptide fragments can be used to competitively inhibit Urb-ctf from binding to DNA or from forming dimers. Antibodies can also be used to modulate the biological activity a polypeptide in a lysate or other cell-free form. Antisense Urb-ctf can also be used as test agents to modulate gene expression.

Markers

The polynucleotides of the present invention can be used with other markers, especially breast cancer markers, to identity, detect, stage, diagnosis, determine, prognosticate, treat, etc., tissue, diseases and conditions, etc, of the breast cancer. Markers can be polynucleotides, polypeptides, antibodies, ligands, specific binding partners, etc. The targets for such markers include, but are not limited genes and polypeptides that are selective for cell types present in the breast cancer. The targets for such markers include, but are not limited genes and polypeptides that are selective for cell types present in the breast. Specific targets include, BRCA1, BRCA2, ATM, PTEN/MMAC1 (e.g., Ali et al., *J. Natl. Cancer Inst.*, 91:1922–1932, 1999), MLH2, MSH2, TP53 (e.g., Done et al., *Cancer Res.*, 58:785–789, 1998), STK11, myc, cyclin D1 (e.g., Weinstat-Saslow et al., *Nature Med.*, 1:1257–1260, 1995), c-erb-B2, keratins, such as 5/6 and 8/18.

Therapeutics

Selective polynucleotides, polypeptides, and specific-binding partners thereto, can be utilized in therapeutic applications, especially to treat diseases and conditions of breast cancer. Useful methods include, but are not limited to, immunotherapy (e.g., using specific-binding partners to polypeptides), vaccination (e.g., using a selective polypeptide or a naked DNA encoding such polypeptide), protein or polypeptide replacement therapy, gene therapy (e.g., germ-line correction, antisense), etc.

Various immunotherapeutic approaches can be used. For instance, unlabeled antibody that specifically recognizes a tissue-specific antigen can be used to stimulate the body to destroy or attack the cancer, to cause down-regulation, to produce complement-mediated lysis, to inhibit cell growth, etc., of target cells which display the antigen, e.g., analogously to how c-erbB-2 antibodies are used to treat breast cancer. In addition, antibody can be labeled or conjugated to enhance its deleterious effect, e.g., with radionuclides and other energy emitting entitities, toxins, such as ricin, exotoxin A (ETA), and diphtheria, cytotoxic or cytostatic agents, immunomodulators, chemotherapeutic agents, etc. See, e.g., U.S. Pat. No. 6,107,090.

An antibody or other specific-binding partner can be conjugated to a second molecule, such as a cytotoxic agent, and used for targeting the second molecule to a tissue-antigen positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624–2636). Examples of cytotoxic agents include, but are not limited to, antimetabolites, alkylating agents, anthracyclines, antibiotics, anti-mitotic agents, radioisotopes and chemotherapeutic agents. Further examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, 1-dehydrotestosterone, diptheria toxin, Pseudomonas exotoxin (PE) A, PE40, abrin, elongation factor-2 and glucocorticoid. Techniques for conjugating therapeutic agents to antibodies are well.

In addition to immunotherapy, polynucleotides and polypeptides can be used as targets for non-immunotherapeutic applications, e.g., using compounds which interfere with function, expression (e.g., antisense as a therapeutic agent), assembly, etc. RNA interference can be used in vivtro and in vivo to silence Urb-ctf when its expression contributes to a disease (but also for other purposes, e.g., to identify the gene's function to change a developmental pathway of a cell, etc.). See, e.g., Sharp and Zamore, *Science,* 287:2431–2433, 2001; Grishok et al., *Science,* 287:2494, 2001.

Delivery of therapeutic agents can be achieved according to any effective method, including, liposomes, viruses, plasmid vectors, bacterial delivery systems, orally, systemically, etc. Therapeutic agents of the present invention can be administered in any form by any effective route, including, e.g., oral, parenteral, enteral, intraperitoneal, topical, transdermal (e.g., using any standard patch), ophthalmic, nasally, local, non-oral, such as aerosal, inhalation, subcutaneous, intramuscular, buccal, sublingual, rectal, vaginal, intra-arterial, and intrathecal, etc. They can be administered alone, or in combination with any ingredient(s), active or inactive.

In addition to therapeutics, per se, the present invention also relates to methods of treating a disease of breast cancer showing altered expression of Urb-ctf, comprising, e.g., administering to a subject in need thereof a therapeutic agent which is effective for regulating expression of said Urb-ctf and/or which is effective in treating said disease. The term "treating" is used conventionally, e.g., the management or care of a subject for the purpose of combating, alleviating, reducing, relieving, improving the condition of, etc., of a disease or disorder. Diseases or disorders which can be treated in accordance with the present invention include, but are not limited to breast cancer. By the phrase "altered expression," it is meant that the disease is associated with a mutation in the gene, or any modification to the gene (or corresponding product) which affects its normal function. Thus, expression of Urb-ctf refers to, e.g., transcription, translation, splicing, stability of the mRNA or protein product, activity of the gene product, differential expression, etc.

Any agent which "treats" the disease can be used. Such an agent can be one which regulates the expression of the Urb-ctf. Expression refers to the same acts already mentioned, e.g. transcription, translation, splicing, stability of the mRNA or protein product, activity of the gene product, differential expression, etc. For instance, if the condition was a result of a complete deficiency of the gene product, administration of gene product to a patient would be said to treat the disease and regulate the gene's expression. Many other possible situations are possible, e.g., where the gene is aberrantly expressed, and the therapeutic agent regulates the aberrant expression by restoring its normal expression pattern. For Urb-ctf in cancer, agents can down-regulate the gene, or inhibit the activity of the protein product in activating gene transcription.

Antisense

Antisense polynucleotide (e.g., RNA) can also be prepared from a polynucleotide according to the present invention, preferably an anti-sense to a sequence of SEQ ID NO 1. Antisense polynucleotide can be used in various ways, such as to regulate or modulate expression of the polypeptides they encode, e.g., inhibit their expression, for in situ hybridization, for therapeutic purposes, for making targeted mutations (in vivo, triplex, etc.) etc. For guidance on administering and designing anti-sense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708. An antisense polynucleotides can be operably linked to an expression control sequence. A total length of about 35 bp can be used in cell culture with cationic liposomes to facilitate cellular uptake, but for in vivo use, preferably shorter oligonucleotides are administered, e.g. 25 nucleotides.

Antisense polynucleotides can comprise modified, non-naturally-occurring nucleotides and linkages between the nucleotides (e.g., modification of the phosphate-sugar backbone; methyl phosphonate, phosphorothioate, or phosphorodithioate linkages; and 2'-O-methyl ribose sugar units), e.g., to enhance in vivo or in vitro stability, to confer nuclease resistance, to modulate uptake, to modulate cellular distribution and compartmentalization, etc. Any effective nucleotide or modification can be used, including those already mentioned, as known in the art, etc., e.g., disclosed in U.S. Pat. Nos. 6,133,438; 6,127,533; 6,124,445; 6,121,437; 5,218,103 (e.g., nucleoside thiophosphoramidites); 4,973,679; Sproat et al., "2'-O-Methyloligoribonucleotides: synthesis and applications," Oligonucleotides and Analogs A Practical Approach, Eckstein (ed.), IRL Press, Oxford, 1991, 49–86; Iribarren et al., "2'-O-Alkyl Oligoribonucleotides as Antisense Probes," Proc. Natl. Acad. Sci. USA, 1990, 87, 7747–7751; Cotton et al., "2'-O-methyl, 2'-O-ethyl oligoribonucleotides and phosphorothioate oligodeoxyribonucleotides as inhibitors of the in vitro U7 snRNP-dependent mRNA processing event," Nucl. Acids Res., 1991, 19, 2629–2635.

Arrays

The present invention also relates to an ordered array of polynucleotide probes and specific-binding partners (e.g., antibodies) for detecting the expression of Urb-ctf in a sample, comprising, one or more polynucleotide probes or specific binding partners associated with a solid support, wherein each probe is specific for Urb-ctf, and the probes comprise a nucleotide sequence of SEQ ID NO 1 which is specific for said gene, a nucleotide sequence having sequence identity to SEQ ID NO 1 which is specific for said gene or polynucleotide, or complements thereto, or a specific-binding partner which is specific for Urb-ctf.

The phrase "ordered array" indicates that the probes are arranged in an identifiable or position-addressable pattern, e.g., such as the arrays disclosed in U.S. Pat. Nos. 6,156,501, 6,077,673, 6,054,270, 5,723,320, 5,700,637, WO09919711, WO00023803. The probes are associated with the solid support in any effective way. For instance, the probes can be bound to the solid support, either by polymerizing the probes on the substrate, or by attaching a probe to the substrate. Association can be, covalent, electrostatic, noncovalent, hydrophobic, hydrophilic, noncovalent, coordination, adsorbed, absorbed, polar, etc. When fibers or hollow filaments are utilized for the array, the probes can fill the hollow orifice, be absorbed into the solid filament, be attached to the surface of the orifice, etc. Probes can be of any effective size, sequence identity, composition, etc., as already discussed.

Ordered arrays can further comprise polynucleotide probes or specific-binding partners which are specific for other genes, including genes specific for breast cancer or disorders associated with breast cancer.

Transgenic Animals

The present invention also relates to transgenic animals comprising Urb-ctf genes. Such genes, as discussed in more detail below, include, but are not limited to, functionally-disrupted genes, mutated genes, ectopically or selectively-expressed genes, inducible or regulatable genes, etc. These transgenic animals can be produced according to any suitable technique or method, including homologous recombination, mutagenesis (e.g., ENU, Rathkolb et al., Exp. Physiol., 85(6):635–644, 2000), and the tetracycline-regulated gene expression system (e.g., U.S. Pat. No. 6,242,667). The term "gene" as used herein includes any part of a gene, i.e., regulatory sequences, promoters, enhancers, exons, introns, coding sequences, etc. The Urb-ctf nucleic acid present in the construct or transgene can be naturally-occurring wild-type, polymorphic, or mutated.

Along these lines, polynucleotides of the present invention can be used to create transgenic animals, e.g. a non-human animal, comprising at least one cell whose genome comprises a functional disruption of Urb-ctf. By the phrases "functional disruption" or "functionally disrupted," it is meant that the gene does not express a biologically-active product. It can be substantially deficient in at least one functional activity coded for by the gene. Expression of a polypeptide can be substantially absent, i.e., essentially undetectable amounts are made. However, polypeptide can also be made, but which is deficient in activity, e.g., where only an amino-terminal portion of the gene product is produced.

The transgenic animal can comprise one or more cells. When substantially all its cells contain the engineered gene, it can be referred to as a transgenic animal "whose genome comprises" the engineered gene. This indicates that the endogenous gene loci of the animal has been modified and substantially all cells contain such modification.

Functional disruption of the gene can be accomplished in any effective way, including, e.g., introduction of a stop codon into any part of the coding sequence such that the resulting polypeptide is biologically inactive (e.g., because it lacks a catalytic domain, a ligand binding domain, etc.), introduction of a mutation into a promoter or other regulatory sequence that is effective to turn it off, or reduce transcription of the gene, insertion of an exogenous sequence into the gene which inactivates it (e.g., which disrupts the production of a biologically-active polypeptide or which disrupts the promoter or other transcriptional machinery), deletion of sequences from the Urb-ctf gene, etc. Examples of transgenic animals having functionally disrupted genes are well known, e.g., as described in U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. A transgenic animal which comprises the functional disruption can also be referred to as a "knock-out" animal, since the biological activity of its Urb-ctf genes has been "knocked-out." Knock-outs can be homozygous or heterozygous.

For creating functional disrupted genes, and other gene mutations, homologous recombination technology is of special interest since it allows specific regions of the genome to be targeted. Using homologous recombination methods, genes can be specifically-inactivated, specific mutations can be introduced, and exogenous sequences can be introduced at specific sites. These methods are well known in the art, e.g., as described in the patents above. See, also, Robertson, Biol. Reproduc., 44(2):238–245, 1991. Generally, the genetic engineering is performed in an embryonic stem (ES) cell, or other pluripotent cell line (e.g., adult stem cells, EG cells), and that genetically-modified cell (or nucleus) is used to create a whole organism. Nuclear transfer can be used in combination with homologous recombination technologies.

For example, the Urb-ctf locus can be disrupted in mouse ES cells using a positive-negative selection method (e.g., Mansour et al., Nature, 336:348–352, 1988). In this method, a targeting vector can be constructed which comprises a part of the gene to be targeted. A selectable marker, such as neomycin resistance genes, can be inserted into a Urb-ctf exon present in the targeting vector, disrupting it. When the vector recombines with the ES cell genome, it disrupts the function of the gene. The presence in the cell of the vector can be determined by expression of neomycin resistance. See, e.g., U.S. Pat. No. 6,239,326. Cells having at least one functionally disrupted gene can be used to make chimeric and germline animals, e.g., animals having somatic and/or germ cells comprising the engineered gene. Homozygous knock-out animals can be obtained from breeding heterozygous knock-out animals. See, e.g., U.S. Pat. No. 6,225,525.

A transgenic animal, or animal cell, lacking one or more functional Urb-ctf genes can be useful in a variety of applications, including, as an animal model for breast cancer diseases, for drug screening assays, for making a cell deficient in Urb-ctf to study the contribution of it and other transcription factors, as a source of tissues deficient in Urb-ctf activity, and any of the utilities mentioned in any issued U.S. Patent on transgenic animals, including, U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. For instance, Urb-ctf deficient animal cells can be utilized to study transcriptional regulatory activity. Breast cancer cells display a variety of activities which are responsive to extracellular and intracellular signals. By knocking-out transcription factors, e.g., one at a time, the physiological pathways using transcriptional regulatory activity can be dissected out and identified.

The present invention also relates to non-human, transgenic animal whose genome comprises recombinant Urb-ctf nucleic acid operatively linked to an expression control sequence effective to express said coding sequence, e.g., in breast tissue. such a transgenic animal can also be referred to as a "knock-in" animal since an exogenous gene has been introduced, stably, into its genome.

A recombinant Urb-ctf nucleic acid refers to a gene which has been introduced into a target host cell and optionally modified, such as cells derived from animals, plants, bacteria, yeast, etc. A recombinant Urb-ctf includes completely synthetic nucleic acid sequences, semi-synthetic nucleic acid sequences, sequences derived from natural sources, and chimeras thereof. "Operable linkage" has the meaning used through the specification, i.e., placed in a functional relationship with another nucleic acid. When a gene is operably linked to an expression control sequence, as explained above, it indicates that the gene (e.g., coding sequence) is joined to the expression control sequence (e.g., promoter) in such a way that facilitates transcription and translation of the coding sequence. As described above, the phrase "genome" indicates that the genome of the cell has been modified. In this case, the recombinant Urb-ctf has been stably integrated into the genome of the animal. The Urb-ctf nucleic acid in operable linkage with the expression control sequence can also be referred to as a construct or transgene.

Any expression control sequence can be used depending on the purpose. For instance, if selective expression is desired, then expression control sequences which limit its expression can be selected. These include, e.g., tissue or cell-specific promoters, introns, enhancers, etc. For various methods of cell and tissue-specific expression, see, e.g., U.S. Pat. Nos. 6,215,040, 6,210,736, and 6,153,427. These also include the endogenous promoter, i.e., the coding sequence can be operably linked to its own promoter. Inducible and regulatable promoters can also be utilized.

The present invention also relates to a transgenic animal which contains a functionally disrupted and a transgene stably integrated into the animals genome. Such an animal can be constructed using combinations any of the above- and below-mentioned methods. Such animals have any of the aforementioned uses, including permitting the knock-out of the normal gene and its replacement with a mutated gene. Such a transgene can be integrated at the endogenous gene locus so that the functional disruption and "knock-in" are carried out in the same step.

In addition to the methods mentioned above, transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology, cloning methods, nuclear transfer methods. See, also, e.g., U.S. Pat. Nos. 4,736,866; 4,873,191; 4,873,316; 5,082,779; 5,304,489; 5,174,986; 5,175,384; 5,175,385; 5,221,778; Gordon et al., Proc. Natl. Acad. Sci., 77:7380–7384, 1980; Palmiter et al., Cell, 41:343–345, 1985; Palmiter et al., Ann. Rev. Genet., 20:465–499, 1986; Askew et al., Mol. Cell. Bio., 13:4115–4124, 1993; Games et al. Nature, 373:523–527, 1995; Valancius and Smithies, Mol. Cell. Bio., 11:1402–1408, 1991; Stacey et al., Mol. Cell. Bio., 14:1009–1016, 1994; Hasty et al., Nature, 350:243–246, 1995; Rubinstein et al., Nucl. Acid Res., 21:2613–2617, 1993; Cibelli et al., Science, 280:1256–1258, 1998. For guidance on recombinase excision systems, see, e.g., U.S. Pat. Nos. 5,626,159, 5,527,695, and 5,434,066. See also, Orban, P. C., et al., "Tissue- and Site-Specific DNA Recombination in Transgenic Mice," Proc. Natl. Acad. Sci. USA, 89:6861–6865 (1992); O'Gorman, S., et al., "Recombinase-Mediated Gene Activation and Site-Specific Integration in Mammalian Cells," Science, 251:1351–1355 (1991); Sauer, B., et al., "Cre-stimulated recombination at loxP-Containing DNA sequences placed into the mammalian genome," Polynucleotides Research, 17(1):147–161 (1989); Gagneten, S. et al. (1997) Nucl. Acids Res. 25:3326–3331; Xiao and Weaver (1997) Nucl. Acids Res. 25:2985–2991; Agah, R. et al. (1997) J. Clin. Invest. 100:169–179; Barlow, C. et al. (1997) Nucl. Acids Res. 25:2543–2545; Araki, K. et al. (1997) Nucl. Acids Res. 25:868–872; Mortensen, R. N. et al. (1992) Mol. Cell. Biol. 12:2391–2395 (G418 escalation method); Lakhlani, P. P. et al. (1997) Proc. Natl. Acad. Sci. USA 94:9950–9955 ("hit and run"); Westphal and Leder (1997) Curr. Biol. 7:530–533 (transposon-generated "knock-out" and "knock-in"); Templeton, N. S. et al. (1997) Gene Ther. 4:700–709 (methods for efficient gene targeting, allowing for a high frequency of homologous recombination events, e.g., without selectable markers); PCT International Publication WO 93/22443 (functionally-disrupted).

A polynucleotide according to the present invention can be introduced into any non-human animal, including a non-human mammal, mouse (Hogan et al., *Manipulating the Mouse Embryo: A Laboratory Manual, Cold Spring Harbor Laboratory*, Cold Spring Harbor, N.Y., 1986), pig (Hammer et al., Nature, 315:343–345, 1985), sheep (Hammer et al., Nature, 315:343–345, 1985), cattle, rat, or primate. See also, e.g., Church, 1987, Trends in Biotech. 5:13–19; Clark et al., Trends in Biotech. 5:20–24, 1987); and DePamphilis et al., BioTechniques, 6:662–680, 1988. Transgenic animals can be produced by the methods described in U.S. Pat. No. 5,994,618, and utilized for any of the utilities described therein.

Database

The present invention also relates to electronic forms of polynucleotides, polypeptides, etc., of the present invention, including computer-readable medium (e.g., magnetic, optical, etc., stored in any suitable format, such as flat files or hierarchical files) which comprise such sequences, or fragments thereof, e-commerce-related means, etc. Along these lines, the present invention relates to methods of retrieving gene sequences from a computer-readable medium, comprising, one or more of the following steps in any effective order, e.g., selecting a cell or gene expression profile, e.g., a profile that specifies that said gene is differentially expressed in breast cancer, and retrieving said differentially expressed gene sequences, where the gene sequences consist of the genes represented by SEQ ID NO 1.

A "gene expression profile" means the list of tissues, cells, etc., in which a defined gene is expressed (i.e, transcribed and/or translated). A "cell expression profile" means the genes which are expressed in the particular cell type. The profile can be a list of the tissues in which the gene is expressed, but can include additional information as well, including level of expression (e.g., a quantity as compared or normalized to a control gene), and information on temporal (e.g., at what point in the cell-cycle or developmental program) and spatial expression. By the phrase "selecting a gene or cell expression profile," it is meant that a user decides what type of gene or cell expression pattern he is interested in retrieving, e.g., he may require that the gene is differentially expressed in a tissue, or he may require that the gene is not expressed in blood, but must be expressed in breast cancer. Any pattern of expression preferences may be selected. The selecting can be performed by any effective method. In general, "selecting" refers to the process in which a user forms a query that is used to search a database of gene expression profiles. The step of retrieving involves searching for results in a database that correspond to the query set forth in the selecting step. Any suitable algorithm can be utilized to perform the search query, including algorithms that look for matches, or that perform optimization between query and data. The database is information that has been stored in an appropriate storage medium, having a suitable computer-readable format. Once results are retrieved, they can be displayed in any suitable format, such as HTML.

For instance, the user may be interested in identifying genes that are differentially expressed in a breast cancer. He may not care whether small amounts of expression occur in other tissues, as long as such genes are not expressed in peripheral blood lymphocytes. A query is formed by the user to retrieve the set of genes from the database having the desired gene or cell expression profile. Once the query is inputted into the system, a search algorithm is used to interrogate the database, and retrieve results.

The present invention also relates to methods of selecting a breast cancer marker from a database comprising polynucleotide sequences, comprising displaying, in a computer-readable medium, a polynucleotide sequence or polypeptide sequence for human Urb-ctf of claim 1, or complements to the polynucleotides sequence, wherein said displayed sequences have been retrieved from said database upon selection by a user. The phrase "upon selection by a user" indicates that a user of the database has specified or directed a search or other retrieval feature that results in the retrieval and display of the target sequences. For example, the user could ask the database to display polynucleotides or polypeptides expressed in breast cancer by inputting an appropriate inquiry. The user could also input sequence information, and request the display of any sequences in the database that match the inputted sequence information. One or more sequences can be displayed at a time in response to any user inquiry.

Advertising, Licensing, etc., Methods

The present invention also relates to methods of advertising, licensing, selling, purchasing, brokering, etc., genes, polynucleotides, specific-binding partners, antibodies, etc., of the present invention. Methods can comprises, e.g., displaying a Urb-ctf gene, Urb-ctf polypeptide, or antibody specific for Urb-ctf in a printed or computer-readable medium (e.g., on the Web or Internet), accepting an offer to purchase said gene, polypeptide, or antibody.

Other

A polynucleotide, probe, polypeptide, antibody, specific-binding partner, etc., according to the present invention can be isolated. The term "isolated" means that the material is in a form in which it is not found in its original environment or in nature, e.g., more concentrated, more purified, separated from component, etc. An isolated polynucleotide includes, e.g., a polynucleotide having the sequenced separated from the chromosomal DNA found in a living animal, e.g., as the complete gene, a transcript, or a cDNA. This polynucleotide can be part of a vector or inserted into a chromosome (by specific gene-targeting or by random integration at a position other than its normal position) and still be isolated in that it is not in a form that is found in its natural environment. A polynucleotide, polypeptide, etc., of the present invention can also be substantially purified. By substantially purified, it is meant that polynucleotide or polypeptide is separated and is essentially free from other polynucleotides or polypeptides, i.e., the polynucleotide or polypeptide is the primary and active constituent. A polynucleotide can also be a recombinant molecule. By "recombinant," it is meant that the polynucleotide is an arrangement or form which does not occur in nature. For instance, a recombinant molecule comprising a promoter sequence would not encompass the naturally-occurring gene, but would include the promoter operably linked to a coding sequence not associated with it in nature, e.g., a reporter gene, or a truncation of the normal coding sequence.

The term "marker" is used herein to indicate a means for detecting or labeling a target. A marker can be a polynucleotide (usually referred to as a "probe"), polypeptide (e.g., an antibody conjugated to a detectable label), PNA, or any effective material.

The topic headings set forth above are meant as guidance where certain information can be found in the application, but are not intended to be the only source in the application where information on such topic can be found. Reference materials For other aspects of the polynucleotides, reference is made to standard textbooks of molecular biology. See, e.g., Hames et al., *Polynucleotide Hybridization*, IL Press, 1985; Davis et al., *Basic Methods in Molecular Biology*, Elsevier Sciences Publishing, Inc., New York, 1986; Sambrook et al., *Molecular Cloning*, CSH Press, 1989; Howe, *Gene Cloning and Manipulation*, Cambridge University Press, 1995; Ausubel et al., *Current Protocols in Molecular Biology*, John Wiley & Sons, Inc., 1994–1998.

The preceding description, utilize the present invention to its fullest extent. The preceding preferred specific embodiments are, therefore, to be construed as merely illustrative, and not limiting the remainder of the disclosure in any way whatsoever. The entire disclosure of all applications, patents and publications, cited above and, in the FIGURE are hereby incorporated by reference in their entirety.

What is claimed is:

1. An isolated polynucleotide, comprising a polynucleotide sequence which codes without interruption for human Urb-ctf comprising amino acids 1–614 as set forth in SEQ ID NO 2, or the complete complement thereto.

2. An isolated polynucleotide of claim 1, comprising the polynucleotide sequence from nucleotide positions 78–1922 as set forth in SEQ ID NO 1, or the complete complement thereto.

3. An isolated human polynucleotide, comprising a polynucleotide sequence which codes without interruption for a full-length human Urb-crf having 614 amino acids, which has transcriptional regulatory activity, and which hybridizes to the complete complement of SEQ ID NO: 1 from nucleotide positions 78–1922 under high stringency conditions comprising overnight incubation in 5×SSC, 0.5% SDS, 100 µg/ml denatured salmon sperm DNA and 50% formamide, at 42° C., followed by washing in 0.1% SSC and 0.1% SDS for 30 min at 65° C.

4. An isolated polynucleotide consisting of a polynucleotide sequence selected from SEQ ID NO 1 wherein said polynucleotide comprises at least 15 nucleotides and codes for a fragment of SEQ ID NO:2 which comprises
   amino acid 38 of SEQ ID NO 2,
   amino acid 68 of SEQ ID NO 2,
   amino acids 76–77 of SEQ ID NO 2,
   amino acid 119 of SEQ ID NO 2,
   amino acid 143–144 of SEQ ID NO 2,
   amino acid 161 of SEQ ID NO 2,
   amino acid 583 of SEQ ID NO 2, or
   amino acid 606 of SEQ ID NO 2; or
   the complete complement thereof.

5. An isolated polynucleotide of claim 4, which is a polynucleotide coding for coding for amino acids 1–263 of SEQ ID NO 2 or 459–614 of SEQ ID NO 2, or a the complete complement thereof.

6. An isolated polynucleotide of claim 4, wherein said polynucleotide is effective in a polymerase chain reaction.

7. An isolated polynucleotide of claim 4, which codes for a polypeptide comprising at least eight amino acids in length.

8. An isolated polynucleotide of claim 1, comprising the polynucleotide sequence from nucleotide positions 1–4372 as set forth in SEQ ID NO 1, or the complete complement thereto.

9. An isolated polynucleotide of claim 4, which comprises at least 24 nucleotides.

10. An isolated polynucleotide of claim 4, which comprises at least 30 nucleotides.

11. An isolated polynucleotide of claim 4, which comprises at least 45 nucleotides.

12. A method of producing human Urb-ctf polypeptide, comprising
    expressing a polynucleotide of claim 1 which codes without interruption for said polypeptide and which is operably linked to an expression control sequence under conditions effective to achieve production of said polypeptide coded for by said polynucleotide.

13. A method of producing human Urb-ctf polypeptide, comprising
    expressing a polynucleotide of claim 1 which codes without interruption for said polypeptide and which is operably linked to an expression control sequence under conditions effective to achieve production of said polypeptide coded for by said polynucleotide.

14. A method of producing human Urb-ctf polypeptide, comprising
    expressing a polynucleotide of claim 3 which codes without interruption for said polypeptide and which is operably linked to an expression control sequence under conditions effective to achieve production of said polypeptide coded for by said polynucleotide.

15. A method of producing human Urb-ctf polypeptide, comprising:
    expressing a polynucleotide of claim 8 which codes without interruption for said polypeptide and which is operably linked to an expression control sequence under conditions effective to achieve production of said polypeptide coded for by said polynucleotide.

* * * * *

UNITED STATES PATENT AND TRADEMARK OFFICE
CERTIFICATE OF CORRECTION

PATENT NO. : 7,053,193 B2 Page 1 of 1
APPLICATION NO. : 10/054935
DATED : May 30, 2006
INVENTOR(S) : Sun et al.

It is certified that error appears in the above-identified patent and that said Letters Patent is hereby corrected as shown below:

Column 47, line 12, reads "Urb-crf" should read -- Urb-ctf --
Column 47, line 35, reads "coding for coding for amino" should read -- coding for amino --
Column 47, line 36, reads "or a the" should read -- or the --
Column 48, line 21, reads "of claim 1" should read -- of claim 2 --

Signed and Sealed this

Nineteenth Day of December, 2006

JON W. DUDAS
*Director of the United States Patent and Trademark Office*

SEQUENCE LISTING

<160> NUMBER OF SEQ ID NOS: 4

<210> SEQ ID NO 1
<211> LENGTH: 4372
<212> TYPE: DNA
<213> ORGANISM: Homo sapiens
<220> FEATURE:
<221> NAME/KEY: CDS
<222> LOCATION: (78)..(1922)
<223> OTHER INFORMATION:

<400> SEQUENCE: 1

```
cagtcctcga ccccccgcac ctcgcccctt ccccaccccc tcctccgcct cggtgcccgg      60
cgctgctccg gaccact atg acc atg aga tcc gcg gtg ttc aag gcg gcc        110
                   Met Thr Met Arg Ser Ala Val Phe Lys Ala Ala
                    1               5                  10 gcg gcc cct gcc ggc ggc aat cct gag cag cga ctg gac tac gag cgg      158
Ala Ala Pro Ala Gly Gly Asn Pro Glu Gln Arg Leu Asp Tyr Glu Arg
            15                  20                  25 gct gcg gcg ctg ggc ggg ccc gag gac gag cct ggg gcg gcc gaa gcc      206
Ala Ala Ala Leu Gly Gly Pro Glu Asp Glu Pro Gly Ala Ala Glu Ala
        30                  35                  40 cac ttc ctc ccc cgg cac cgt aag ctc aag gag ccg ggg ccc ccg ctg      254
His Phe Leu Pro Arg His Arg Lys Leu Lys Glu Pro Gly Pro Pro Leu
    45                  50                  55 gcc tcc tcc cag ggc ggg agc ccc gcg cct tcc ccg gcc ggc tgc ggc      302
Ala Ser Ser Gln Gly Gly Ser Pro Ala Pro Ser Pro Ala Gly Cys Gly
60                  65                  70                  75 ggc aag ggc cgg ggc ttg tta ctc ccg gcc ggg gcg gcc ccc ggg cag      350
Gly Lys Gly Arg Gly Leu Leu Leu Pro Ala Gly Ala Ala Pro Gly Gln
                80                  85                  90 cag gaa gag agc tgg ggc ggt tcg gtg ccc ttg ccc tgt ccg ccc ccg      398
Gln Glu Glu Ser Trp Gly Gly Ser Val Pro Leu Pro Cys Pro Pro Pro
                95                 100                 105 gcc acc aag caa gcc ggc att ggg ggg gag cct gcc gca gcc gga gcc      446
Ala Thr Lys Gln Ala Gly Ile Gly Gly Glu Pro Ala Ala Ala Gly Ala
            110                 115                 120 ggc tgc agc ccc cgg ccc aag tat cag gcg gtg ctg ccc att cag acg      494
Gly Cys Ser Pro Arg Pro Lys Tyr Gln Ala Val Leu Pro Ile Gln Thr
        125                 130                 135 ggc tct ctc gtg gcg gcg gcc aaa gag cct acg ccc tgg gct ggg gac      542
Gly Ser Leu Val Ala Ala Ala Lys Glu Pro Thr Pro Trp Ala Gly Asp
    140                 145                 150                 155 aag ggt ggg gcg gcc tcc ccc gct gcc acc gcc tcg gac ccg gcg gga      590
Lys Gly Gly Ala Ala Ser Pro Ala Ala Thr Ala Ser Asp Pro Ala Gly
                160                 165                 170 ccc cca cca cta cct ctg ccc ggg ccg cca ccc ctc gcg ccc acc gcc      638
Pro Pro Pro Leu Pro Leu Pro Gly Pro Pro Pro Leu Ala Pro Thr Ala
            175                 180                 185 acc gcc ggg acc ctg gcg gcc agc gag ggc aga tgg aag agt atg agg      686
Thr Ala Gly Thr Leu Ala Ala Ser Glu Gly Arg Trp Lys Ser Met Arg
        190                 195                 200 aag agc cct ctc ggg ggt ggt ggc ggc tcg gga gcc tcc agt cag gcc      734
Lys Ser Pro Leu Gly Gly Gly Gly Ser Gly Ala Ser Ser Gln Ala
    205                 210                 215 gcc tgc ctc aaa cag atc ctt ctg ctg caa ttg gac ctc atc gaa cag      782
Ala Cys Leu Lys Gln Ile Leu Leu Leu Gln Leu Asp Leu Ile Glu Gln
220                 225                 230                 235 cag cag cag cag ctg cag gcc aag gaa aag gag atc gag gag ctg aag      830
```

```
                  Gln Gln Gln Gln Leu Gln Ala Lys Glu Lys Glu Ile Glu Glu Leu Lys
                              240                 245                 250 tca gag aga gac acg ctc ctt gct cgg att gaa cgt atg gaa agg cgg               878
Ser Glu Arg Asp Thr Leu Leu Ala Arg Ile Glu Arg Met Glu Arg Arg
            255                 260                 265 atg cag ctg gta aag aag gat aac gag aaa gaa agg cac aag ctg ttt               926
Met Gln Leu Val Lys Lys Asp Asn Glu Lys Glu Arg His Lys Leu Phe
        270                 275                 280 cag ggc tat gaa act gaa gag aga gag gaa aca gag cta tct gag aaa               974
Gln Gly Tyr Glu Thr Glu Glu Arg Glu Glu Thr Glu Leu Ser Glu Lys
    285                 290                 295 att aaa ctg gag tgc cag ccg gag ctt tcc gag aca tcc cag act ctg              1022
Ile Lys Leu Glu Cys Gln Pro Glu Leu Ser Glu Thr Ser Gln Thr Leu
300                 305                 310                 315 cct ccc aag ccc ttc tca tgt ggg cgg agt gga aag gga cat aaa agg              1070
Pro Pro Lys Pro Phe Ser Cys Gly Arg Ser Gly Lys Gly His Lys Arg
                320                 325                 330 aaa tcc cca ttt gga agt aca gaa aga aag act cct gtt aaa aag ctg              1118
Lys Ser Pro Phe Gly Ser Thr Glu Arg Lys Thr Pro Val Lys Lys Leu
            335                 340                 345 gct cct gaa ttt tca aaa gtc aaa aca aaa act cct aag cac tct cct              1166
Ala Pro Glu Phe Ser Lys Val Lys Thr Lys Thr Pro Lys His Ser Pro
        350                 355                 360 att aaa gag gaa ccc tgt ggt tcc tta tct gaa act gtt tgt aaa cgt              1214
Ile Lys Glu Glu Pro Cys Gly Ser Leu Ser Glu Thr Val Cys Lys Arg
    365                 370                 375 gaa ttg agg agc caa gaa acc cca gaa aag ccc cgg tct tca gtg gac              1262
Glu Leu Arg Ser Gln Glu Thr Pro Glu Lys Pro Arg Ser Ser Val Asp
380                 385                 390                 395 acc cca cca aga ctc tcc act ccc caa aag gga ccc agc acc cat ccc              1310
Thr Pro Pro Arg Leu Ser Thr Pro Gln Lys Gly Pro Ser Thr His Pro
                400                 405                 410 aag gag aaa gcc ttc tca agt gag ata gaa gat ttg ccg tac ctt tcc              1358
Lys Glu Lys Ala Phe Ser Ser Glu Ile Glu Asp Leu Pro Tyr Leu Ser
            415                 420                 425 acc aca gaa atg tat ttg tgt cgt tgg cac cag cct ccc cca tca ccg              1406
Thr Thr Glu Met Tyr Leu Cys Arg Trp His Gln Pro Pro Pro Ser Pro
        430                 435                 440 tta cca tta cgg gaa tcc tct cca aag aag gag gag act gta gca agg              1454
Leu Pro Leu Arg Glu Ser Ser Pro Lys Lys Glu Glu Thr Val Ala Arg
    445                 450                 455 tgt ctg atg cca tca agt gtt gca gga gaa act tca gtc ttg gct gtt              1502
Cys Leu Met Pro Ser Ser Val Ala Gly Glu Thr Ser Val Leu Ala Val
460                 465                 470                 475 cct tct tgg agg gac cac tca gta gag cct cta agg gac cca aat cct              1550
Pro Ser Trp Arg Asp His Ser Val Glu Pro Leu Arg Asp Pro Asn Pro
                480                 485                 490 tca gac ctt ttg gag aac ctg gat gac agt gtg ttt tcg aag cgg cat              1598
Ser Asp Leu Leu Glu Asn Leu Asp Asp Ser Val Phe Ser Lys Arg His
            495                 500                 505 gca aaa ctg gag ctg gat gag aag aga agg aaa aga tgg gat att cag              1646
Ala Lys Leu Glu Leu Asp Glu Lys Arg Arg Lys Arg Trp Asp Ile Gln
        510                 515                 520 agg atc agg gaa caa aga att tta cag cga ctg cag ctc aga atg tat              1694
Arg Ile Arg Glu Gln Arg Ile Leu Gln Arg Leu Gln Leu Arg Met Tyr
    525                 530                 535 aaa aag aaa gga att cag gaa tct gag cct gag gtt acc tca ttt ttc              1742
Lys Lys Lys Gly Ile Gln Glu Ser Glu Pro Glu Val Thr Ser Phe Phe
540                 545                 550                 555
```

-continued

| | | |
|---|---|---|
| cct gag cca gat gat gtt gaa agt ttg atg att acc ccc ttc ttg cct<br>Pro Glu Pro Asp Asp Val Glu Ser Leu Met Ile Thr Pro Phe Leu Pro<br>560                 565                 570 | | 1790 |
| gtt gta gca ttt gga cga cca tta cca aaa tta act cca cag aat ttt<br>Val Val Ala Phe Gly Arg Pro Leu Pro Lys Leu Thr Pro Gln Asn Phe<br>575                 580                 585 | | 1838 |
| gag cta ccc tgg ttg gat gag cgt agc cga tgc aga ttg gag atc cag<br>Glu Leu Pro Trp Leu Asp Glu Arg Ser Arg Cys Arg Leu Glu Ile Gln<br>590                 595                 600 | | 1886 |
| aag aag caa aca cct cac cgg acg tgt agg aaa tag ctgtgctggc<br>Lys Lys Gln Thr Pro His Arg Thr Cys Arg Lys<br>605                 610 | | 1932 |
| aagaaccctg tcttcagata gttgtagcat gccattcccg agagtggcag agacctgtat | | 1992 |
| atgtgacctt tgtcctcaca tatgttatca ctcgctgata atacccttc atacttcctt | | 2052 |
| gactttgttt tcattactct gatttcacaa aaactctttc attcggctaa ttgtgagtta | | 2112 |
| tggagggtga ttgggatttc ttttcccttt tttgggaaat gggctctcaa gctaaagcta | | 2172 |
| taggatggca gattcagaag tttcaggggt ctgtttctat acatttgcct atgttaaagg | | 2232 |
| ggtaaagggg ctctcttcat tagacatgtg aagatgaag cagcccttc ctttagagct | | 2292 |
| gtgcctgcat ggcactcttc tcaccctggt acaccctcct tatagtgggt atagtgattt | | 2352 |
| ttaaccctaa aataaaacaa acaacctcac catgagcttt aggaccagaa gaggaatgac | | 2412 |
| aagtgaagcg atgaagcaag ccatcttcac agagtagaaa agacatcgga gagttggtag | | 2472 |
| ataactgtct gaaagatag ttgttcattt gaaactattc tgtgatacag tcatgtggga | | 2532 |
| agggatgttt ggctgtgatt atttttcag ttaatggata acaatttctt tactgctcaa | | 2592 |
| aaaccaaaat cttggaaaa gaaagtgggg atggttagtt tcagaacaag ttacagctgt | | 2652 |
| aaacaaaagc acttagtatt tgggatggca tgccaaaacc tgtataaatg tccttgtatc | | 2712 |
| acatcacttc tcaagtattc cttcattggg cttcatcctt ttagcagaac tcttggtggt | | 2772 |
| gggatagaga cttagggagg gtaggggag agtgtggaaa taggtgcttc ctttggctgg | | 2832 |
| caaatgtcta catcttgaaa caaacagatg tacctaatga gcttctccat tcactttgta | | 2892 |
| aaaataattt gtatgtgtac catcttggtc ctctcccctc ccgttttgtt aaaatatcag | | 2952 |
| gatagcactc ccaggccact ttggtctcag tgtaagatcc ctattaacta tctgaaagga | | 3012 |
| aaatagagcc aagacctctg gtctcaaata tataggaatt gcctttcttt agtcttcagg | | 3072 |
| actattgtgt gaaacaagt aggggtctaa tctcctagaa ggtaggggct tttatcctta | | 3132 |
| aagagaatat gtccccagat tattagcact tttagaggag aagccaaggt atgtagggtg | | 3192 |
| tgtggctggc ccatcagtgg agcacgaaga gagaatggga taccattgtg ggaagagaag | | 3252 |
| aaaagttcct caggggcctc ccactgctaa agttttttgt gagatgttga tctgtgcttc | | 3312 |
| ctggatttga cttttaaagg aattattctg gcagcacatg tagtattctt ggatgatctt | | 3372 |
| gctgctctta tttctccttt tgtgtgtgtg tgtgtgtgtg tgtggctatg ggttttcatt | | 3432 |
| tgtaactcca tctgcttagg agagtgggct ctctataagg gaacctgctg taaacttcat | | 3492 |
| tgcagcaagg atgtagagag aaataggact taattccact aggggctctc atctcacacc | | 3552 |
| ttaaggagga gatttctaga aaaactgggc cagatttct ttgttctcca tcattttaat | | 3612 |
| gtggcaggct gttcagtttt cttactctta cctatgtgat atttcttcgt aacgtgtcca | | 3672 |
| aaaagaaaaa agacccaatc agtgtctctt gactttgttc tttgatccct cagtttcttc | | 3732 |
| ttgatttcag catgtgtcgg gttcctaatt ttgggtatga gttagcaaat ttaaccattg | | 3792 |
| tgtttgtgcc ctacccaggg gactccccag tttctgactt gaagtagact gagaagaatc | | 3852 |

-continued

```
cacgaggtgc tatctggcca gatttaagta gattctattt ccttggttct ccctctccct    3912
gaggacctct tattttattg tcccctcttc taggttaatt ctcctttgat ttgactttgt    3972
tgagaaggag gttggacagt agattagcaa agttccaagt gcaaaattac agtgtgttag    4032
agtgtggggg gaaaattagt cttattttc cctacatggg atacaacact gtgaattcaa     4092
tcttcaactg aaggccctgc agttctccta aacatagtt gtttgttttt ctttaacaaa     4152
gtttaagcta gtgttaataa attaaaaaaa attgcttgtc tgtctacttc agctttgttt    4212
tatgcccatt tcatattgtt gtctgtgttg taattcataa cttttgatac catttctgat    4272
gtgtaaaatt ggttgtcttg taaatatctt ataaagagtt caattgtaaa taaactattg    4332
tggctgttaa aaaaaaaaaa aaaaaaaaaa aaaaaaaaa                           4372
```

<210> SEQ ID NO 2
<211> LENGTH: 614
<212> TYPE: PRT
<213> ORGANISM: Homo sapiens

<400> SEQUENCE: 2

```
Met Thr Met Arg Ser Ala Val Phe Lys Ala Ala Ala Pro Ala Gly
 1               5                  10                  15

Gly Asn Pro Glu Gln Arg Leu Asp Tyr Glu Arg Ala Ala Leu Gly
                20                  25                  30

Gly Pro Glu Asp Glu Pro Gly Ala Ala Glu Ala His Phe Leu Pro Arg
                35                  40                  45

His Arg Lys Leu Lys Glu Pro Gly Pro Pro Leu Ala Ser Ser Gln Gly
 50                  55                  60

Gly Ser Pro Ala Pro Ser Pro Ala Gly Cys Gly Gly Lys Gly Arg Gly
 65                  70                  75                  80

Leu Leu Leu Pro Ala Gly Ala Ala Pro Gly Gln Gln Glu Glu Ser Trp
                85                  90                  95

Gly Gly Ser Val Pro Leu Pro Cys Pro Pro Ala Thr Lys Gln Ala
                100                 105                 110

Gly Ile Gly Gly Glu Pro Ala Ala Gly Ala Gly Cys Ser Pro Arg
                115                 120                 125

Pro Lys Tyr Gln Ala Val Leu Pro Ile Gln Thr Gly Ser Leu Val Ala
 130                 135                 140

Ala Ala Lys Glu Pro Thr Pro Trp Ala Gly Asp Lys Gly Gly Ala Ala
 145                 150                 155                 160

Ser Pro Ala Ala Thr Ala Ser Asp Pro Ala Gly Pro Pro Leu Pro
                165                 170                 175

Leu Pro Gly Pro Pro Pro Leu Ala Pro Thr Ala Thr Ala Gly Thr Leu
                180                 185                 190

Ala Ala Ser Glu Gly Arg Trp Lys Ser Met Arg Lys Ser Pro Leu Gly
                195                 200                 205

Gly Gly Gly Gly Ser Gly Ala Ser Ser Gln Ala Ala Cys Leu Lys Gln
                210                 215                 220

Ile Leu Leu Leu Gln Leu Asp Leu Ile Glu Gln Gln Gln Gln Gln Leu
 225                 230                 235                 240

Gln Ala Lys Glu Lys Glu Ile Glu Glu Leu Lys Ser Glu Arg Asp Thr
                245                 250                 255

Leu Leu Ala Arg Ile Glu Arg Met Glu Arg Arg Met Gln Leu Val Lys
                260                 265                 270

Lys Asp Asn Glu Lys Glu Arg His Lys Leu Phe Gln Gly Tyr Glu Thr
```

```
                275                 280                 285
Glu Glu Arg Glu Glu Thr Glu Leu Ser Glu Lys Ile Lys Leu Glu Cys
    290                 295                 300
Gln Pro Glu Leu Ser Glu Thr Ser Gln Thr Leu Pro Lys Pro Phe
305                 310                 315                 320
Ser Cys Gly Arg Ser Gly Lys Gly His Lys Arg Lys Ser Pro Phe Gly
                325                 330                 335
Ser Thr Glu Arg Lys Thr Pro Val Lys Lys Leu Ala Pro Glu Phe Ser
                340                 345                 350
Lys Val Lys Thr Lys Thr Pro Lys His Ser Pro Ile Lys Glu Glu Pro
                355                 360                 365
Cys Gly Ser Leu Ser Glu Thr Val Cys Lys Arg Glu Leu Arg Ser Gln
    370                 375                 380
Glu Thr Pro Glu Lys Pro Arg Ser Ser Val Asp Thr Pro Pro Arg Leu
385                 390                 395                 400
Ser Thr Pro Gln Lys Gly Pro Ser Thr His Pro Lys Glu Lys Ala Phe
                405                 410                 415
Ser Ser Glu Ile Glu Asp Leu Pro Tyr Leu Ser Thr Thr Glu Met Tyr
                420                 425                 430
Leu Cys Arg Trp His Gln Pro Pro Ser Pro Leu Pro Leu Arg Glu
    435                 440                 445
Ser Ser Pro Lys Lys Glu Glu Thr Val Ala Arg Cys Leu Met Pro Ser
    450                 455                 460
Ser Val Ala Gly Glu Thr Ser Val Leu Ala Val Pro Ser Trp Arg Asp
465                 470                 475                 480
His Ser Val Glu Pro Leu Arg Asp Pro Asn Pro Ser Asp Leu Leu Glu
                485                 490                 495
Asn Leu Asp Asp Ser Val Phe Ser Lys Arg His Ala Lys Leu Glu Leu
                500                 505                 510
Asp Glu Lys Arg Arg Lys Arg Trp Asp Ile Gln Arg Ile Arg Glu Gln
                515                 520                 525
Arg Ile Leu Gln Arg Leu Gln Leu Arg Met Tyr Lys Lys Lys Gly Ile
    530                 535                 540
Gln Glu Ser Glu Pro Glu Val Thr Ser Phe Phe Pro Glu Pro Asp Asp
545                 550                 555                 560
Val Glu Ser Leu Met Ile Thr Pro Phe Leu Pro Val Val Ala Phe Gly
                565                 570                 575
Arg Pro Leu Pro Lys Leu Thr Pro Gln Asn Phe Glu Leu Pro Trp Leu
                580                 585                 590
Asp Glu Arg Ser Arg Cys Arg Leu Glu Ile Gln Lys Lys Gln Thr Pro
                595                 600                 605
His Arg Thr Cys Arg Lys
    610

<210> SEQ ID NO 3
<211> LENGTH: 198
<212> TYPE: PRT
<213> ORGANISM: Homo sapiens

<400> SEQUENCE: 3

Met Glu Arg Arg Met Gln Leu Val Lys Lys Asp Asn Glu Lys Glu Arg
1               5                   10                  15

His Lys Leu Phe Gln Gly Tyr Glu Thr Glu Glu Arg Glu Glu Thr Glu
                20                  25                  30
```

-continued

```
Leu Ser Glu Lys Ile Lys Leu Glu Cys Gln Pro Glu Leu Ser Glu Thr
        35                  40                  45
Ser Gln Thr Leu Pro Pro Lys Pro Phe Ser Cys Gly Arg Ser Gly Lys
    50                  55                  60
Gly His Lys Arg Lys Ser Pro Phe Gly Ser Thr Glu Arg Lys Thr Pro
65                  70                  75                  80
Val Lys Lys Leu Ala Pro Glu Phe Ser Lys Val Lys Thr Lys Thr Pro
                85                  90                  95
Lys His Ser Pro Ile Lys Glu Glu Pro Cys Gly Ser Leu Ser Glu Thr
            100                 105                 110
Val Cys Lys Arg Glu Leu Arg Ser Gln Glu Thr Pro Glu Lys Pro Arg
        115                 120                 125
Ser Ser Val Asp Thr Pro Pro Arg Leu Ser Thr Pro Gln Lys Gly Pro
    130                 135                 140
Ser Thr His Pro Lys Glu Lys Ala Phe Ser Ser Glu Ile Glu Asp Leu
145                 150                 155                 160
Pro Tyr Leu Ser Thr Thr Glu Met Tyr Leu Cys Arg Trp His Gln Pro
                165                 170                 175
Pro Pro Ser Pro Leu Pro Leu Arg Glu Ser Ser Pro Lys Lys Glu Glu
            180                 185                 190
Thr Val Ala Ser Lys Ala
        195

<210> SEQ ID NO 4
<211> LENGTH: 616
<212> TYPE: PRT
<213> ORGANISM: Mus musculus

<400> SEQUENCE: 4

Met Thr Met Arg Ser Ala Val Phe Lys Ala Ala Ala Pro Ala Gly
1               5                   10                  15
Gly Asn Pro Glu Gln Arg Leu Asp Tyr Glu Arg Ala Ala Leu Gly
                20                  25                  30
Gly Pro Glu Asp Glu Ser Gly Ala Ala Glu Ala His Phe Leu Pro Arg
        35                  40                  45
His Arg Lys Leu Lys Glu Pro Gly Pro Pro Leu Ala Ser Ser Gln Gly
    50                  55                  60
Gly Ser Pro Ser Pro Ser Pro Ala Gly Cys Gly Gly Lys Gly Arg
65                  70                  75                  80
Gly Leu Leu Leu Pro Ala Gly Ala Ala Pro Gly Gln Gln Glu Glu Ser
                85                  90                  95
Trp Gly Gly Ser Val Pro Leu Pro Cys Pro Pro Ala Thr Lys Gln
            100                 105                 110
Ala Gly Ile Gly Gly Glu Pro Val Ala Ala Gly Ala Gly Cys Ser Pro
        115                 120                 125
Arg Pro Lys Tyr Gln Ala Val Leu Pro Ile Gln Thr Gly Ser Ile Val
    130                 135                 140
Val Ala Ala Ala Lys Glu Pro Thr Pro Trp Ala Gly Asp Lys Gly Gly
145                 150                 155                 160
Ala Ala Pro Pro Ala Ala Thr Ala Ser Asp Pro Ala Gly Pro Pro Pro
                165                 170                 175
Leu Pro Leu Pro Gly Pro Pro Leu Ala Pro Thr Ala Thr Ala Gly
            180                 185                 190
Thr Leu Ala Ala Ser Glu Gly Arg Trp Lys Ser Ile Arg Lys Ser Pro
        195                 200                 205
```

```
Leu Gly Gly Gly Gly Ser Gly Ala Ser Ser Gln Ala Ala Cys Leu
    210                 215                 220
Lys Gln Ile Leu Leu Leu Gln Leu Asp Leu Ile Glu Gln Gln Gln
225                 230                 235                 240
Gln Leu Gln Ala Lys Glu Lys Glu Ile Glu Glu Leu Lys Ser Glu Arg
                    245                 250                 255
Asp Thr Leu Leu Ala Arg Ile Glu Arg Met Glu Arg Arg Met Gln Leu
                260                 265                 270
Val Lys Arg Asp Asn Glu Lys Glu Arg His Lys Leu Leu Gln Gly Tyr
            275                 280                 285
Glu Pro Glu Glu Arg Glu Glu Ala Glu Leu Ser Glu Lys Ile Lys Leu
        290                 295                 300
Glu Arg Gln Pro Glu Leu Cys Glu Thr Ser Gln Ala Leu Pro Ser Lys
305                 310                 315                 320
Pro Phe Ser Cys Gly Arg Ser Gly Lys Gly His Lys Arg Lys Thr Pro
                    325                 330                 335
Phe Gly Asn Thr Glu Arg Lys Asn Pro Val Lys Lys Leu Ala Pro Glu
                340                 345                 350
Phe Ser Lys Val Lys Thr Lys Thr Pro Lys His Ser Pro Ile Lys Glu
            355                 360                 365
Glu Pro Cys Gly Ser Ile Ser Glu Thr Val Cys Lys Arg Glu Leu Arg
        370                 375                 380
Ser Gln Glu Thr Pro Glu Lys Pro Arg Ser Ser Val Asp Thr Pro Pro
385                 390                 395                 400
Arg Leu Ser Thr Pro Gln Lys Gly Pro Ser Thr His Pro Lys Glu Lys
                    405                 410                 415
Ala Phe Ser Ser Glu Met Glu Asp Leu Pro Tyr Leu Ser Thr Thr Glu
                420                 425                 430
Met Tyr Leu Cys Arg Trp His Gln Pro Pro Ser Pro Leu Pro Leu
            435                 440                 445
Arg Glu Ser Ser Pro Lys Lys Glu Glu Thr Val Ala Arg Cys Leu Met
450                 455                 460
Pro Ser Ser Val Ala Gly Glu Thr Ser Val Leu Ala Val Pro Ser Trp
465                 470                 475                 480
Arg Asp His Ser Val Glu Pro Leu Arg Asp Pro Asn Pro Ser Asp Ile
                485                 490                 495
Leu Glu Asn Leu Asp Asp Ser Val Phe Ser Lys Arg His Ala Lys Leu
                500                 505                 510
Glu Leu Asp Glu Lys Arg Arg Lys Arg Trp Asp Ile Gln Arg Ile Arg
            515                 520                 525
Glu Gln Arg Ile Leu Gln Arg Leu Gln Leu Arg Met Tyr Lys Lys Lys
        530                 535                 540
Gly Ile Gln Glu Ser Glu Pro Glu Val Thr Ser Phe Phe Pro Glu Pro
545                 550                 555                 560
Asp Asp Val Glu Ser Leu Leu Ile Thr Pro Phe Leu Pro Val Val Ala
                    565                 570                 575
Phe Gly Arg Pro Leu Pro Lys Leu Ala Pro Gln Asn Phe Glu Leu Pro
                580                 585                 590
Trp Leu Asp Glu Arg Ser Arg Cys Arg Leu Glu Ile Gln Lys Lys His
            595                 600                 605
Thr Pro His Arg Thr Cys Arg Lys
        610                 615
```